(12) United States Patent
Van Der Lelie et al.

(10) Patent No.: US 6,602,666 B2
(45) Date of Patent: *Aug. 5, 2003

(54) RECOMBINANT NUCLEIC ACID SEQUENCES AND METHODS FOR DETERMINING BOTH GENOTOXICITY AND MUTAGENICITY OF A SAMPLE AND THE KINETICS OF THE GENOTOXICITY

(75) Inventors: Daniel Van Der Lelie, Mol (BE); Brigitte Marie Francoise Borremans, Bierbeek (BE); Ann Irma Alice Provoost, Lichtaart (BE); Luc Agnes Louis Jean Bosco Regniers, Dessel (BE); Luc Philipinne Edouard Verschaeve, Brussels (BE)

(73) Assignee: Vlaamse Instelling Technologisch Onderzoek (V.I.T.O.), Mol (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/843,378

(22) Filed: Apr. 25, 2001

(65) Prior Publication Data

US 2003/0003578 A1 Jan. 2, 2003

Related U.S. Application Data

(63) Continuation of application No. 09/171,586, filed on Dec. 2, 1998.

(51) Int. Cl.$^7$ .................................................. C12Q 1/68
(52) U.S. Cl. ..................... 435/6; 435/320.1; 435/252.3; 435/252.33; 536/23.1; 536/24.1
(58) Field of Search ...................... 435/6, 320.1, 252.3, 435/252.33; 536/23.1, 24.1

(56) References Cited

U.S. PATENT DOCUMENTS 5,702,883 A * 12/1997 Imaeda et al. ................. 435/4

FOREIGN PATENT DOCUMENTS

| EP | 0 063 522 | 10/1982 |
|---|---|---|
| EP | 0649905 A1 * | 10/1994 |
| EP | 0 649 905 | 4/1995 |
| WO | WO 84 01388 | 4/1984 |
| WO | WO 92 15687 | 9/1992 |
| WO | WO 94 13831 | 6/1994 |

OTHER PUBLICATIONS

1987, "Nucleotide sequence and LexA refulation of the *Escheria coli* recN gene" Rostas, et al. Nucleic Acid Research, vol. 15, No. 13, pp. 5041–5049.
1994, "Genes V" Lewin, Oxford University Press, pp. 393–396.
1982, "How *Escherichia coli* sets different basal levels in SOS operons" Huisman, et al. Biochemie, vol. 64, pp. 709–712.
1985, "Nucleotide sequence binding specifity of the LexA repressor of *Escherichia coli* K–12" Wertman, et al. J.Bac., vol. 163, No. 1, pp. 376–384.
1983, "Revised methods for the salmonella mutagenicity test" Marion and Ames, Mutation Research, vol. 113, pp. 173–215.
1991, "RecA protein in the SOS response: milestones and mysteries" Witkin, Biochemie, vol. 73, pp. 133–141.
1996, "*Escherichia coli* and Salmonella" Neidhardt, et al., Cellular and molecular biology, 2nd edition, vol. 1.
"The SOS response of *Escherichia coli*" Walker, ASM Press, Washington, p. 1400–1416.
1980, "Nucleortde sequence of the gene ompA coding the other membrane protein II* of *Escherichia coli* K–12" Beck, et al. Nucleic Acids Research, vol. 8, No. 13, pp. 3011.
1985, "Identification of the *Escherichia coli* recN Gene Product as a Major SOS Protein" Finch, et al., Journal of Bacteriology, vol. 164, No. 2, pp. 653–658.
1994, "Detection and classification of metagens: A set of base–specific Salmonella tester strains" Gee, et al. Proc. Natl. Acad. Sci. vol. 91, pp. 11606–11610.
1994, "Evidence for a Novel Pathway in the Degradation of Flourene by *Pseudomonas sp.* Strain F274" Grifoll, et al. Applied and Environmental Microbiology, vol. 60, No. 7, pp. 2438–2449.
1983, "Revised methods for the Salmonella mutagenicity test" Maron, et al. Mutation Research, pp. 173–215.
1977, "Lambdoid Phages that Simplify the Recovery of in vitro Recombinants" Murray, et al., Molec. gen Genet. pp. 53–61.
1985, "Evaluation of the new system (umu–test) for the detection of environmental mutagens and cracinogens" Oda, et al. Mutation Research, pp. 219–229.
1987, "Differential Repression of SOS Genes by Unstable LexA41 (Ts–1) Protein Causes a "Split–phenotype" in *Escherichia coli* K–12" Peterson, et al. Journal of Molecular Biology, pp. 27–40.
1985, "The recN locus of *Escherichia coli* K12: molecular analysis and identification of the gene product" Picksley, et al. Journal Gen Genet, pp. 301–307.
Oct. 1982, "SOS chromotest, a direct assay of induction of an SOS function in *Escherichia coli* K–12 to measure genotoxicity" Quillardet, et al. Proc. Natl. Acad. Sci, USA vol. 79, pp. 5971–5975.
1987, "Nucleotide sequence and LexA regulation of the *Escherichai coli* recN gene" Rodas, et al. Nucleic Acids Research, vol. 15, No. 13.
1991, "DNA binding properties of the LexA repressor" Schnaar, et al. Biochemie, vol. 73, pp. 423–431.

* cited by examiner

*Primary Examiner*—James Ketter
(74) *Attorney, Agent, or Firm*—Merchant & Gould P.C.

(57) ABSTRACT

A recombinant nucleic acid sequence comprising an SOS regulated promoter with an induction ratio higher than 40, said promoter being operatively linked to a reporter encoding nucleic acid sequence encoding a reporter resulting in a signal that can be assayed as light production. A biosensor comprising such a nucleic acid sequence and methods for determining genotoxicity and the presence of multiple genotoxic compounds using such a biosensor are disclosed.

17 Claims, 20 Drawing Sheets

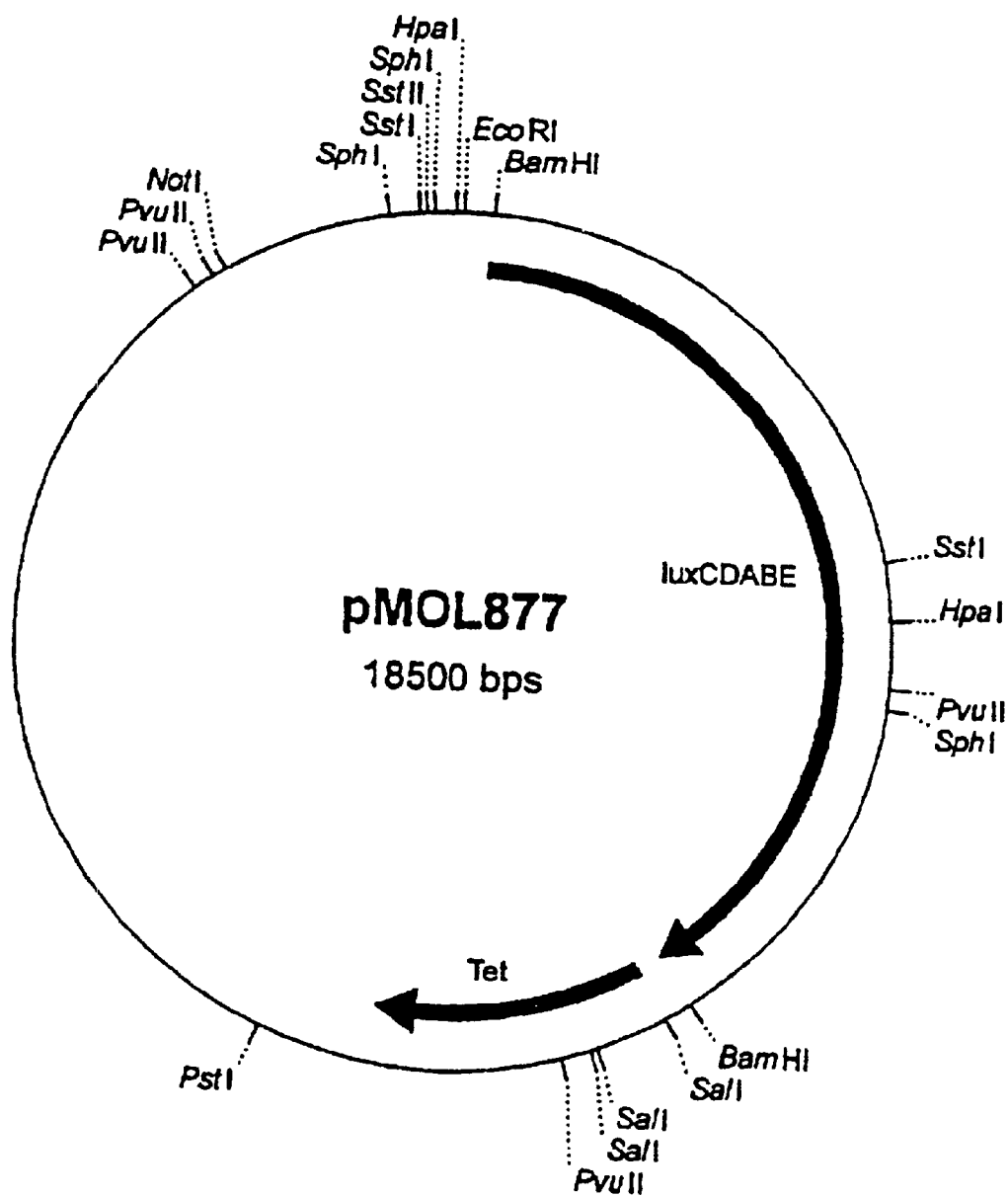

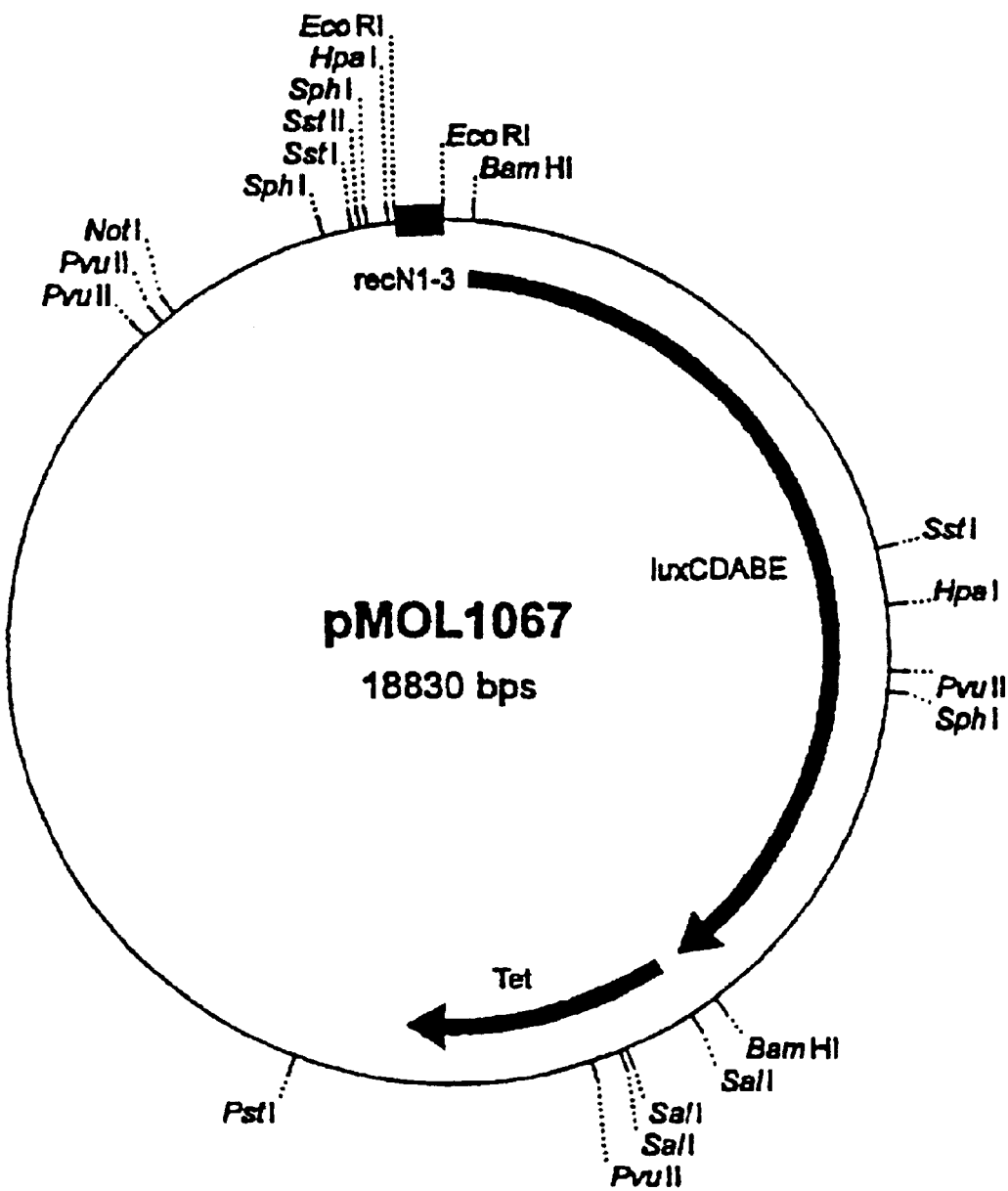

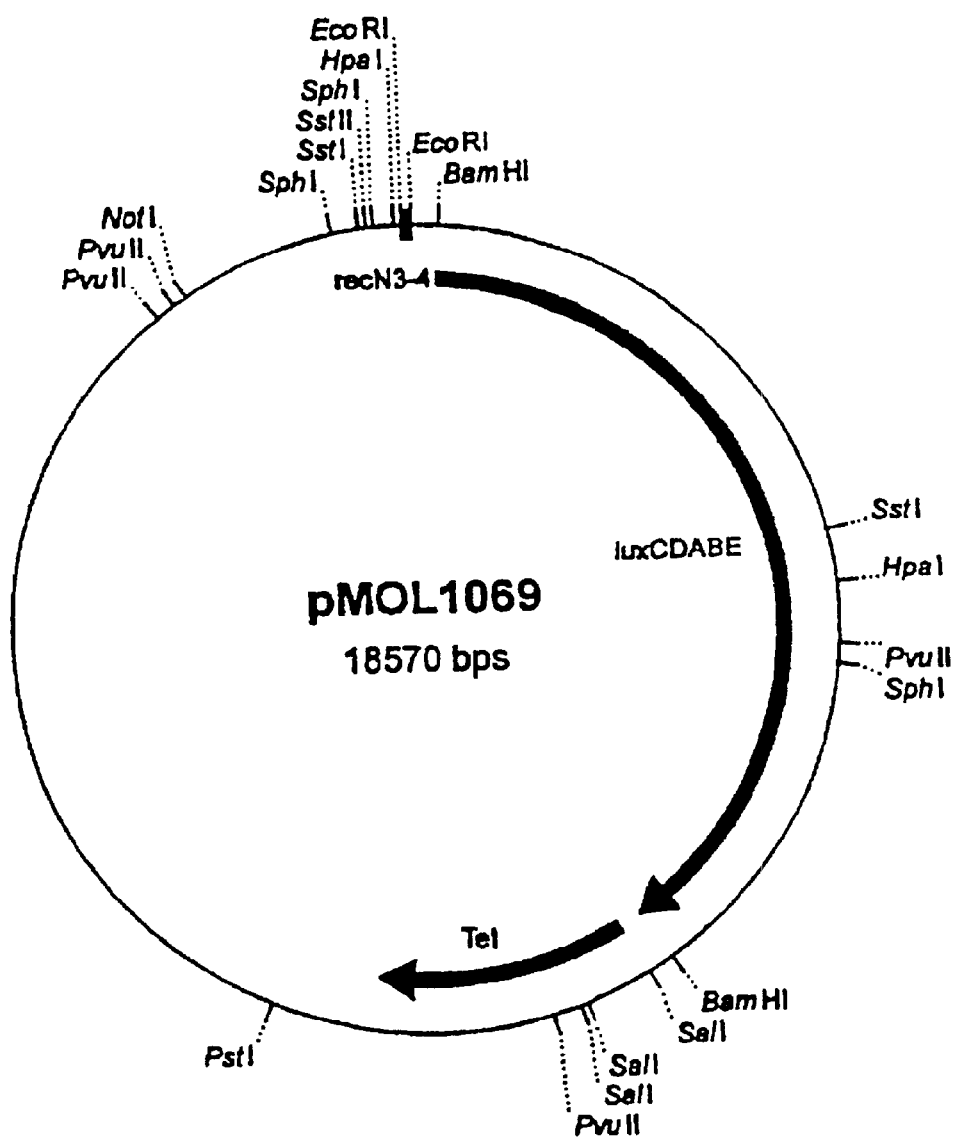

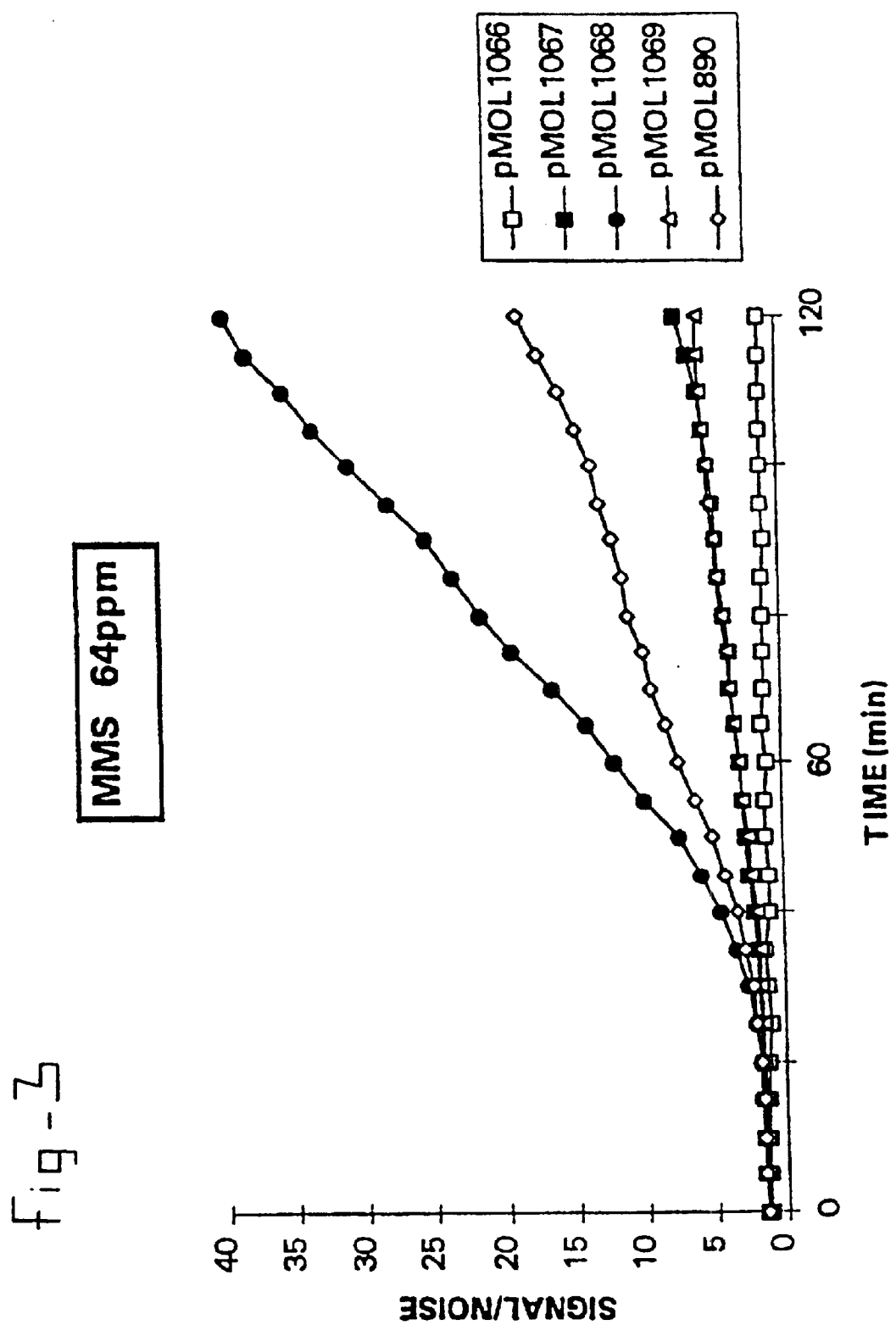

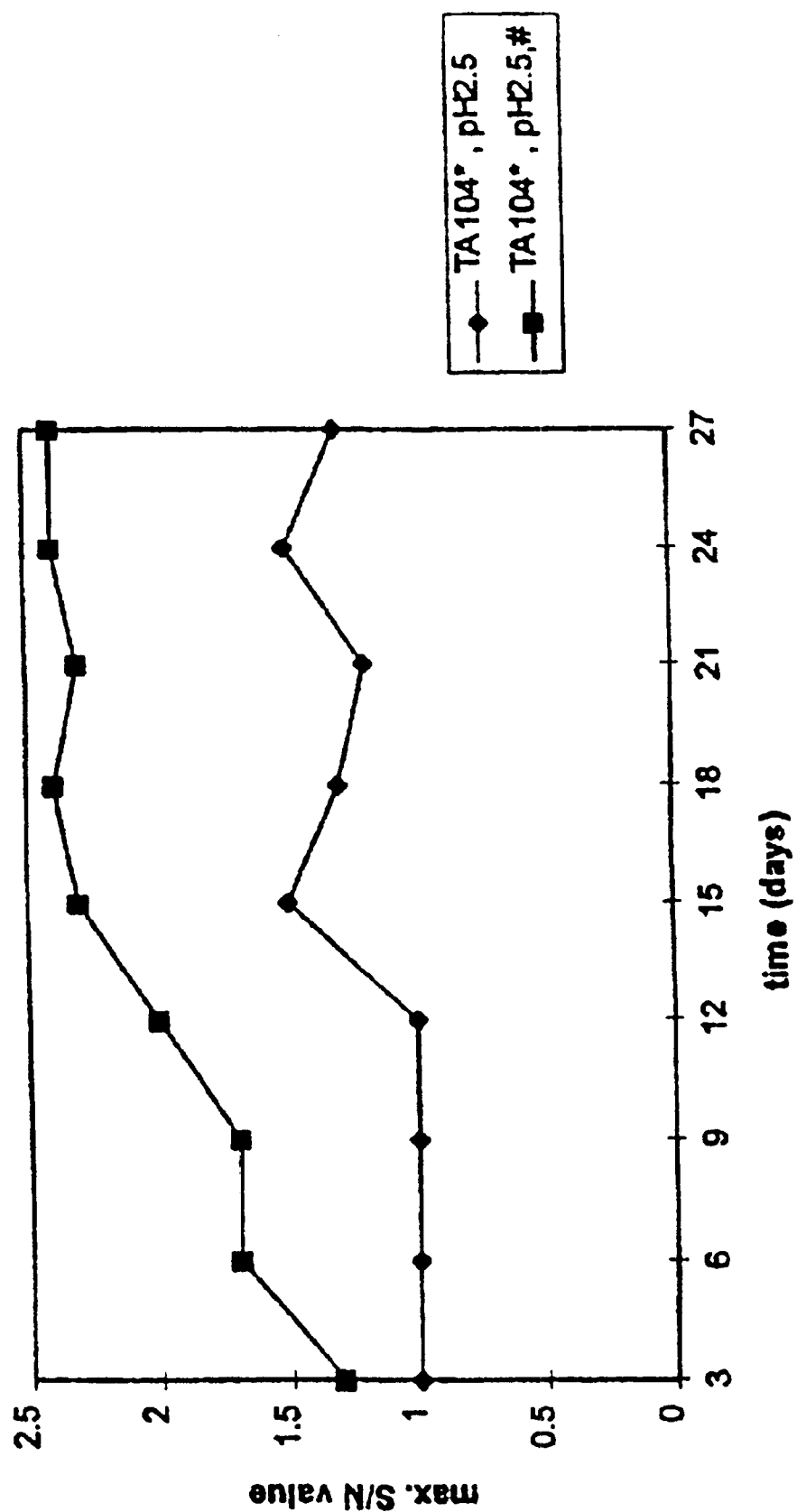

Figure 1B:
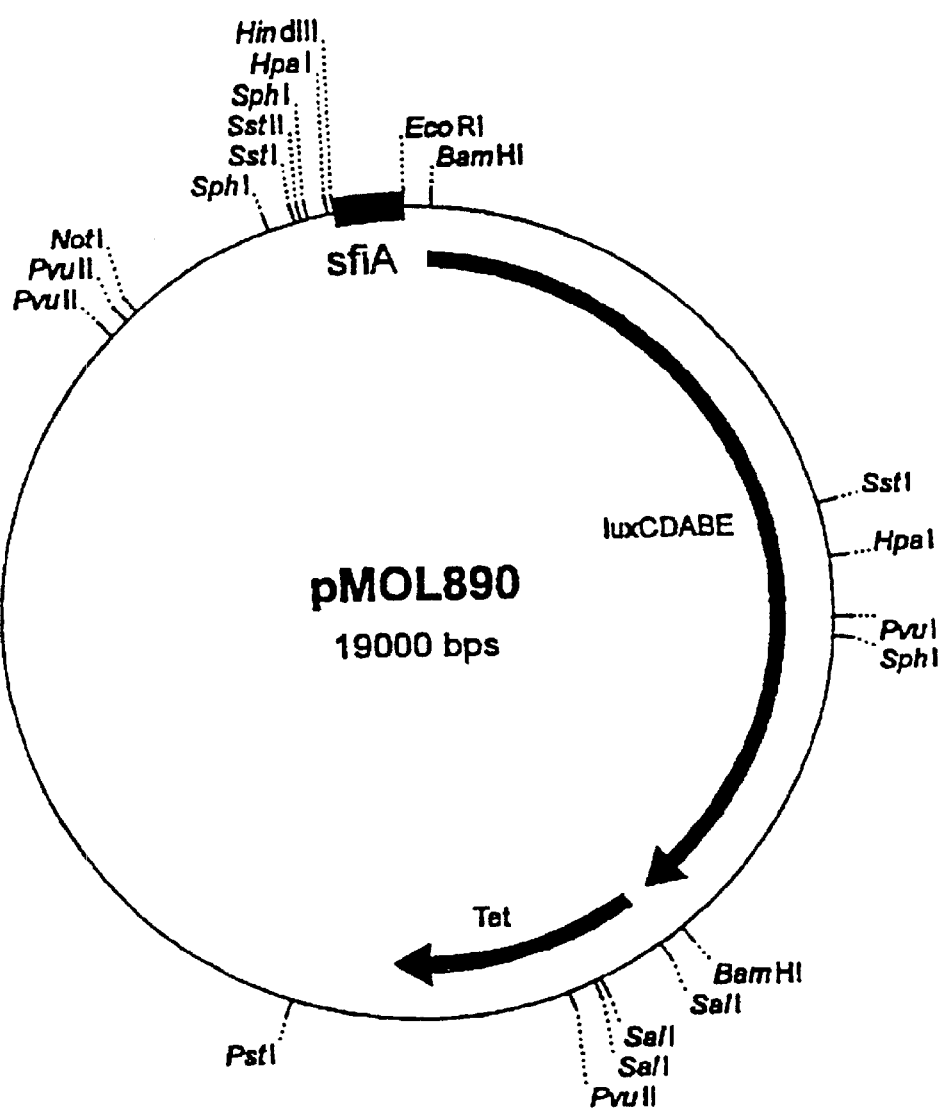
Figure 2A:
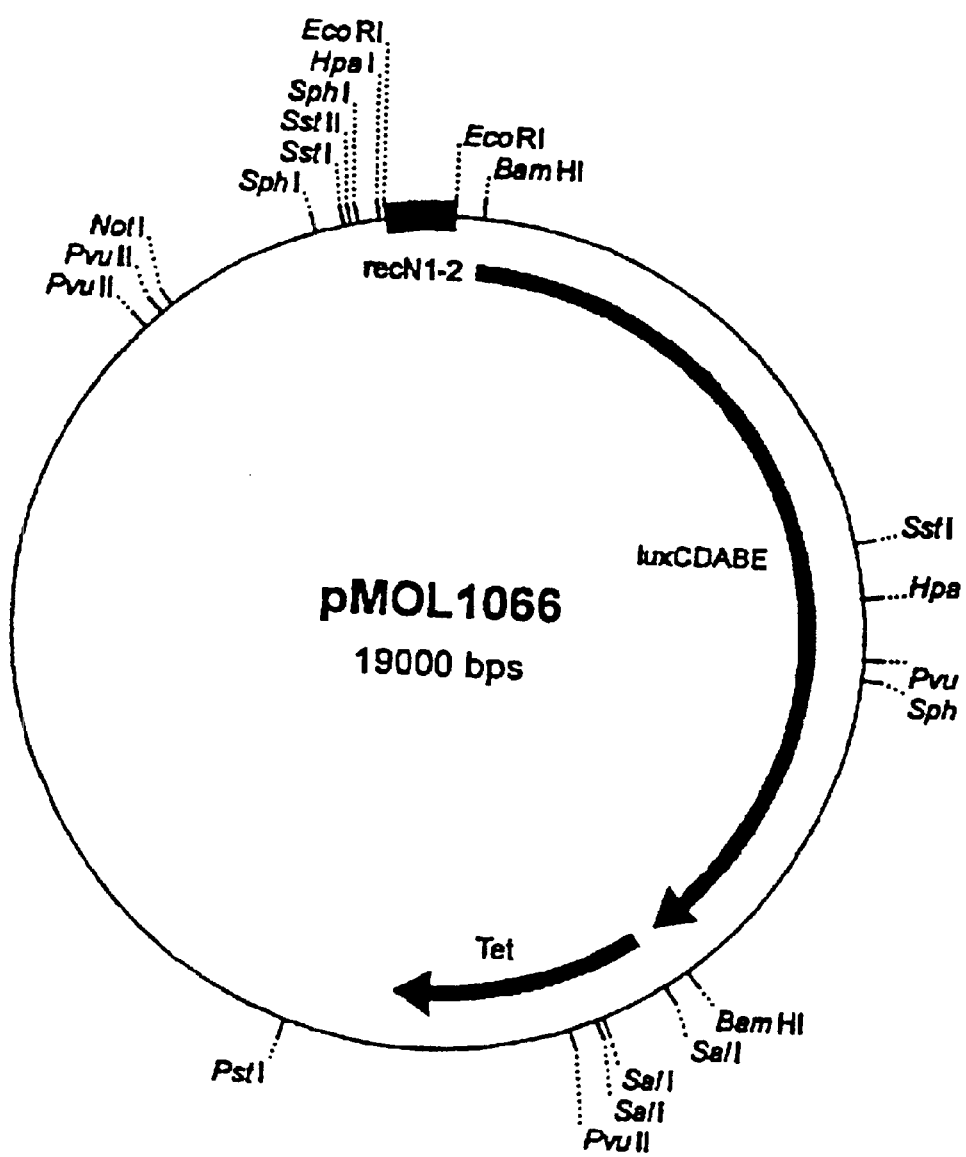
Figure 2C:
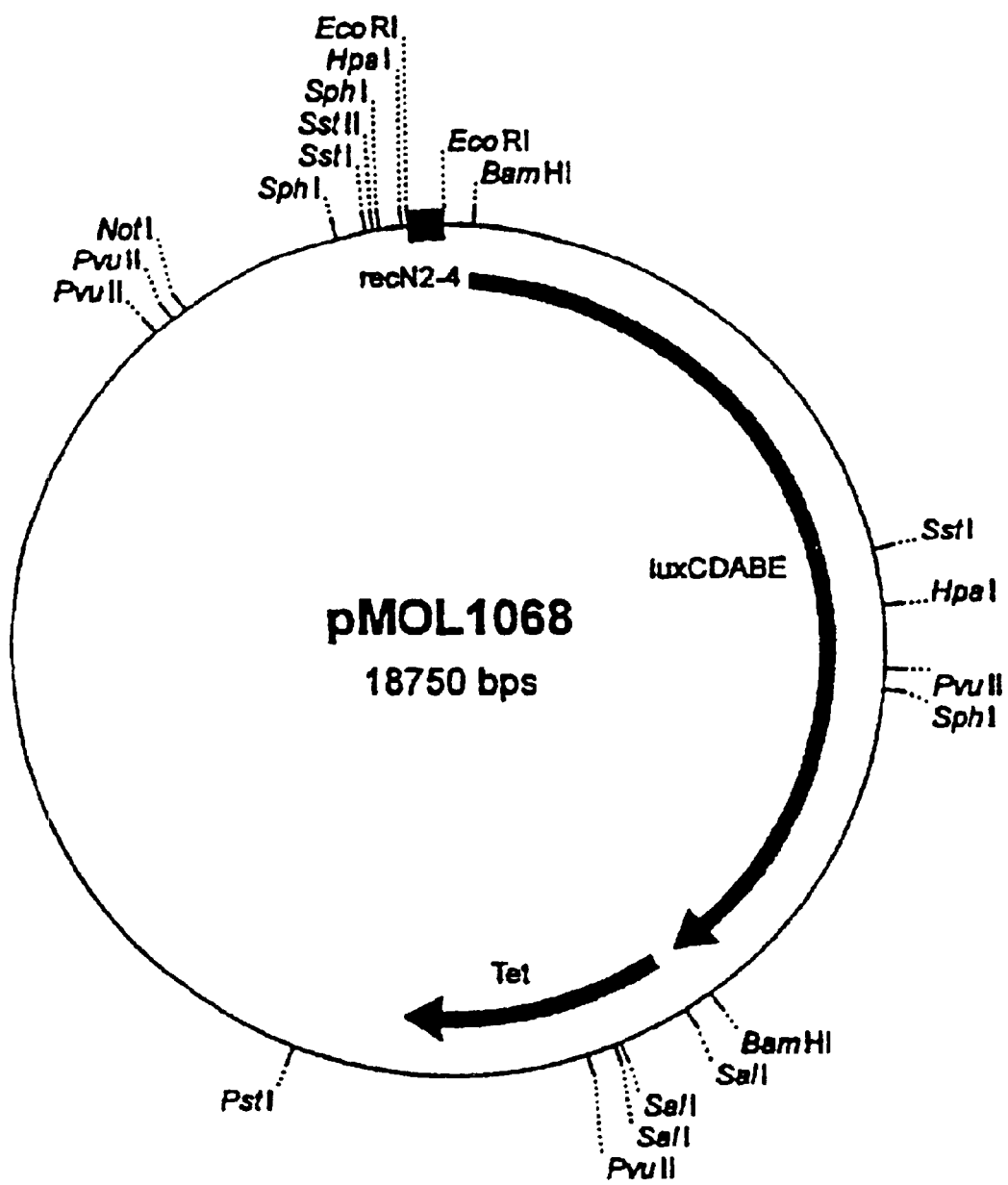

SEQUENCE LISTING

<160> NUMBER OF SEQ ID NOS: 13

<210> SEQ ID NO 1
<211> LENGTH: 38
<212> TYPE: DNA
<213> ORGANISM: Artificial Sequence
<220> FEATURE:
<223> OTHER INFORMATION: sfiA primer 94C97

<400> SEQUENCE: 1
tttaagcttc ccgtcaccaa cgacaaaatt tgcgaggc                    38

<210> SEQ ID NO 2
<211> LENGTH: 29
<212> TYPE: DNA
<213> ORGANISM: Artificial Sequence
<220> FEATURE:
<223> OTHER INFORMATION: sfiA complementary strand primer 94C96

<400> SEQUENCE: 2
aagaattccc gactcagttt ttgttgcgg                              29

<210> SEQ ID NO 3
<211> LENGTH: 51
<212> TYPE: DNA
<213> ORGANISM: Escherichia coli

<400> SEQUENCE: 3
gcctctttac ttgtatataa aaccagttta tactgtacac aataacagta a        51

<210> SEQ ID NO 4
<211> LENGTH: 29
<212> TYPE: DNA
<213> ORGANISM: Artificial Sequence
<220> FEATURE:
<223> OTHER INFORMATION: consensus promoter sequence
<221> NAME/KEY: misc_feature
<222> LOCATION: (7)..(23)
<223> OTHER INFORMATION: any nucleotide combination

<400> SEQUENCE: 4
ttgacannnn nnnnnnnnnn nnntataat                                 29

<210> SEQ ID NO 5
<211> LENGTH: 22
<212> TYPE: DNA
<213> ORGANISM: Artificial Sequence
<220> FEATURE:
<223> OTHER INFORMATION: recN PCR primer 1

<400> SEQUENCE: 5
ctctggaatt cgattaccct gg                                        22

<210> SEQ ID NO 6
<211> LENGTH: 25
<212> TYPE: DNA
<213> ORGANISM: Artificial Sequence
<220> FEATURE:
<223> OTHER INFORMATION: recN PCR primer 2

<400> SEQUENCE: 6
tgtcgaattc agcgcgacca ccgag                                     25

<210> SEQ ID NO 7
<211> LENGTH: 32
<212> TYPE: DNA
<213> ORGANISM: Artificial Sequence
<220> FEATURE:
<223> OTHER INFORMATION: recN PCR primer 3

<400> SEQUENCE: 7
aaagaattct tattgtgtac agtataaact gg                             32

<210> SEQ ID NO 8
<211> LENGTH: 38
<212> TYPE: DNA
<213> ORGANISM: Artificial Sequence
<220> FEATURE:
<223> OTHER INFORMATION: recN PCR primer 4

<400> SEQUENCE: 8 aaagaattc taattttacg ccagcctctt gactgtat                        38

<210> SEQ ID NO 9
<211> LENGTH: 334
<212> TYPE: DNA
<213> ORGANISM: Artificial Sequence
<220> FEATURE:
<223> OTHER INFORMATION: recN1-3 mutant sequence
<221> NAME/KEY: mutation
<222> LOCATION: (329)..(329)
<223> OTHER INFORMATION:
<221> NAME/KEY: mutation
<222> LOCATION: (331)..(331)
<223> OTHER INFORMATION:

<221> NAME/KEY: mutation
<222> LOCATION: (333)..(334)
<223> OTHER INFORMATION:

<400> SEQUENCE: 9

```
gaattcgatt accctggtgc ccatgttccc gcattacgtt gtcagcacga ccactggtca      60
taaacagcag cagcacgatc cgtctgcgtt tttcgcatcg ccgtaacgac ctggaaatca     120
gttgcgacag ccagatagca ctgccgattc aggaaggtga agatgtcctg attcgtcgct     180
gtgattacca tctgaatctg attcatccga aagattacag ttatttcaac acactttaag    240
caccaagctc ggctggtcaa aaaaattatt ctaattttac gccagcctct ttactgtata    300
taaaaccagt ttatactgta cacaataaga attc                                 334
```

<210> SEQ ID NO 10
<211> LENGTH: 249
<212> TYPE: DNA
<213> ORGANISM: Artificial Sequence
<220> FEATURE:
<223> OTHER INFORMATION: recN2-4 mutant sequence
<221> NAME/KEY: mutation
<222> LOCATION: (27)..(27)
<223> OTHER INFORMATION:

<400> SEQUENCE: 10

```
gaattctaat tttacgccag cctcttgact gtatataaaa ccagtttata ctgtacacaa      60
taacagtaat ggttttcat acaggaaacg actatgttgg cacaactgac catcagcaac     120
tttgctatcg ttcgtgagct tgagattgat tttcatagcg gcatgaccgt aataactggc    180
gagaccggcg cgggtaaatc tattgcaata gatgccctcg gtctttgtct cggtggtcgc    240
gctgaattc                                                             249
```

<210> SEQ ID NO 11
<211> LENGTH: 69
<212> TYPE: DNA
<213> ORGANISM: Artificial Sequence
<220> FEATURE:
<223> OTHER INFORMATION: recN3-4 mutant sequence
<221> NAME/KEY: mutation
<222> LOCATION: (27)..(27)
<223> OTHER INFORMATION:
<221> NAME/KEY: mutation
<222> LOCATION: (64)..(64)
<223> OTHER INFORMATION:
<221> NAME/KEY: mutation
<222> LOCATION: (66)..(66)
<223> OTHER INFORMATION:
<221> NAME/KEY: mutation
<222> LOCATION: (68)..(69)
<223> OTHER INFORMATION:

<400> SEQUENCE: 11

```
gaattctaat tttacgccag cctcttgact gtatataaaa ccagtttata ctgtacacaa      60
taagaattc                                                              69
```

<210> SEQ ID NO 12
<211> LENGTH: 2224
<212> TYPE: DNA
<213> ORGANISM: Escherichia coli
<220> FEATURE:
<221> NAME/KEY: CDS
<222> LOCATION: (391)..(2091)
<223> OTHER INFORMATION:
<221> NAME/KEY: -10_signal
<222> LOCATION: (345)..(349)
<223> OTHER INFORMATION:

```
<221> NAME/KEY: -35_signal
<222> LOCATION: (322)..(327)
<223> OTHER INFORMATION:
<221> NAME/KEY: misc_binding
<222> LOCATION: (325)..(341)
<223> OTHER INFORMATION: lexA binding site 1
<221> NAME/KEY: misc_binding
<222> LOCATION: (347)..(363)
<223> OTHER INFORMATION: lexA binding site 2
<221> NAME/KEY: promoter
<222> LOCATION: (317)..(366)
<223> OTHER INFORMATION:

<400> SEQUENCE: 12
ctgcaggcgg tcctattctg accccctctc tggaattcga ttaccctggt gcccatgttc      60
ccgcattacg ttgtcagcac gaccactggt cataaacagc agcagcacga tccgtctgcg     120 ttttttcgcat cgccgtaacg acctggaaat cagttgcgac agccagatag cactgccgat    180
tcaggaaggt gaagatgtcc tgattcgtcg ctgtgattac catctgaatc tgattcatcc     240
gaaagattac agttatttca acacactttta agcaccaagc tcggctggtc aaaaaaatta   300 ttctaattttt acgccagcct ctttactgta tataaaacca gtttatactg tacacaataa   360
cagtaatggt ttttcataca ggaaacgact atg ttg gca caa ctg acc atc agc     414
                                  Met Leu Ala Gln Leu Thr Ile Ser
                                    1               5 aac ttt gct atc gtt cgt gag ctt gag att gat ttt cat agc ggc atg      462
Asn Phe Ala Ile Val Arg Glu Leu Glu Ile Asp Phe His Ser Gly Met
        10                  15                  20 acc gta ata act ggc gag acc ggc gcg ggt aaa tct att gca ata gat      510
Thr Val Ile Thr Gly Glu Thr Gly Ala Gly Lys Ser Ile Ala Ile Asp
 25                  30                  35                  40 gcc ctc ggt ctt tgt ctc ggt ggt cgc gct gaa ttc gac atg gtg cgt      558
Ala Leu Gly Leu Cys Leu Gly Gly Arg Ala Glu Phe Asp Met Val Arg
                 45                  50                  55 acc ggc tgt cgc gct gac ctg tgc gcc cgt ttt tct ctg aaa gat acg      606
Thr Gly Cys Arg Ala Asp Leu Cys Ala Arg Phe Ser Leu Lys Asp Thr
             60                  65                  70 cca gcg cgt ctg cgc tgg ctg gaa gaa aac cag ctt gaa gac ggg cat      654
Pro Ala Arg Leu Arg Trp Leu Glu Glu Asn Gln Leu Glu Asp Gly His
         75                  80                  85 gaa tgt ttg ctt cgt cgc gtg atc agc agc gat ggt cgc tcc cgt ggt      702
Glu Cys Leu Leu Arg Arg Val Ile Ser Ser Asp Gly Arg Ser Arg Gly
     90                  95                 100 ttc atc aac ggt aca gct gtt cct ctg tca caa ctg cgc gaa ctg ggt      750
Phe Ile Asn Gly Thr Ala Val Pro Leu Ser Gln Leu Arg Glu Leu Gly
105                 110                 115                 120 cag ttg ctg att cag atc cat ggt cag cac gct cat caa tta ctc acc      798
Gln Leu Leu Ile Gln Ile His Gly Gln His Ala His Gln Leu Leu Thr
                125                 130                 135 aaa cct gag cac caa aaa ttc ctg ctt gat ggc tat gcc aat gaa acc      846
Lys Pro Glu His Gln Lys Phe Leu Leu Asp Gly Tyr Ala Asn Glu Thr
            140                 145                 150 tct cta ctg cag gaa atg acc gca cgt tat cag ttg tgg cat caa agc      894
Ser Leu Leu Gln Glu Met Thr Ala Arg Tyr Gln Leu Trp His Gln Ser
        155                 160                 165 tgc cgt gac ctc gcg cat cat caa cag tta agt cag gaa cgc gcc gcc      942
Cys Arg Asp Leu Ala His His Gln Gln Leu Ser Gln Glu Arg Ala Ala
    170                 175                 180 cgt gcg gaa ctg ctg caa tac caa tta aaa gaa ctt aac gaa ttt aat      990
Arg Ala Glu Leu Leu Gln Tyr Gln Leu Lys Glu Leu Asn Glu Phe Asn
185                 190                 195                 200
```

| | |
|---|---|
| ccg cag ccc gga gag ttt gaa caa atc gac gaa gag tac aaa cgt ctg<br>Pro Gln Pro Gly Glu Phe Glu Gln Ile Asp Glu Glu Tyr Lys Arg Leu<br>205 210 215 | 1038 |
| gcg aac agc ggt caa ttg ctg acc acc agc cag aat gca ttg gca tta<br>Ala Asn Ser Gly Gln Leu Leu Thr Thr Ser Gln Asn Ala Leu Ala Leu<br>220 225 230 | 1086 |
| atg gcc gac ggt gaa gac gca aac ctg caa agt cag ctt tac acg gct<br>Met Ala Asp Gly Glu Asp Ala Asn Leu Gln Ser Gln Leu Tyr Thr Ala<br>235 240 245 | 1134 |
| aaa caa ctg gtg agc gaa ttg att ggc atg gac agc aaa ctg tcc ggc<br>Lys Gln Leu Val Ser Glu Leu Ile Gly Met Asp Ser Lys Leu Ser Gly<br>250 255 260 | 1182 |
| gta ctt gat atg ctg gaa gaa gct acc atc cag att gct gaa gcc agc<br>Val Leu Asp Met Leu Glu Glu Ala Thr Ile Gln Ile Ala Glu Ala Ser<br>265 270 275 280 | 1230 |
| gat gaa ctg cgc cac tac tgc gat cgt ctg gat ctc gat ccc aac cga<br>Asp Glu Leu Arg His Tyr Cys Asp Arg Leu Asp Leu Asp Pro Asn Arg<br>285 290 295 | 1278 |
| cta ttt gaa ctt gaa cag cgc atc tca aaa cag att tcg ctg gca cgt<br>Leu Phe Glu Leu Glu Gln Arg Ile Ser Lys Gln Ile Ser Leu Ala Arg<br>300 305 310 | 1326 |
| aaa cat cac gtc agc cct gag gca ttg cca cag tat tac cag tcg cta<br>Lys His His Val Ser Pro Glu Ala Leu Pro Gln Tyr Tyr Gln Ser Leu<br>315 320 325 | 1374 |
| ctg gaa gaa cag cag caa ctg gac gat cag gcc gac tca caa gaa acg<br>Leu Glu Glu Gln Gln Gln Leu Asp Asp Gln Ala Asp Ser Gln Glu Thr<br>330 335 340 | 1422 |
| ctt gcg ctg gcg gta acg aaa cat cat cag cag gca ctg gaa atc gcg<br>Leu Ala Leu Ala Val Thr Lys His His Gln Gln Ala Leu Glu Ile Ala<br>345 350 355 360 | 1470 |
| cgc gca tta cac caa caa cgc cag caa tat gca gaa gaa ctt gca cag<br>Arg Ala Leu His Gln Gln Arg Gln Gln Tyr Ala Glu Glu Leu Ala Gln<br>365 370 375 | 1518 |
| ctg atc acc gac agt atg cat gcg ctc tca atg ccg cat ggg cag ttt<br>Leu Ile Thr Asp Ser Met His Ala Leu Ser Met Pro His Gly Gln Phe<br>380 385 390 | 1566 |
| acg atc gat gtt aaa ttt gac gag cat cac ctg ggc gct gac ggt gcc<br>Thr Ile Asp Val Lys Phe Asp Glu His His Leu Gly Ala Asp Gly Ala<br>395 400 405 | 1614 |
| gat cgt att gag ttt cgg gta acc acc aac cca ggt cag cca atg cag<br>Asp Arg Ile Glu Phe Arg Val Thr Thr Asn Pro Gly Gln Pro Met Gln<br>410 415 420 | 1662 |
| cct att gcc aaa gtc gca tcc ggt ggt gaa ttg tcc cgc atc gca ctg<br>Pro Ile Ala Lys Val Ala Ser Gly Gly Glu Leu Ser Arg Ile Ala Leu<br>425 430 435 440 | 1710 |
| gca atc cag gtc atc acg gcg cgt aaa atg gaa acc ccg gca ctg att<br>Ala Ile Gln Val Ile Thr Ala Arg Lys Met Glu Thr Pro Ala Leu Ile<br>445 450 455 | 1758 |
| ttt gat gaa gtg gat gta ggg att agc ggt cca aca gcg gca gtt gtc<br>Phe Asp Glu Val Asp Val Gly Ile Ser Gly Pro Thr Ala Ala Val Val<br>460 465 470 | 1806 |
| ggc aaa ctg ctg cgt caa ctc ggc gaa tca act cag gtg atg tgt gtt<br>Gly Lys Leu Leu Arg Gln Leu Gly Glu Ser Thr Gln Val Met Cys Val<br>475 480 485 | 1854 |
| acc cac ctg cca caa gtc gcg gga tgt ggt cat caa cac tat ttt gtc<br>Thr His Leu Pro Gln Val Ala Gly Cys Gly His Gln His Tyr Phe Val<br>490 495 500 | 1902 |
| agc aaa gaa acc gat ggt gcg atg aca gaa acg cat atg caa tcc ctg<br>Ser Lys Glu Thr Asp Gly Ala Met Thr Glu Thr His Met Gln Ser Leu<br>505 510 515 520 | 1950 |

```
aat aaa aaa gcg cgg tta caa gag ctg gcg cgc ctg ctt gtg gca gtg      1998
Asn Lys Lys Ala Arg Leu Gln Glu Leu Ala Arg Leu Leu Val Ala Val
            525                 530                 535 aag tca cac gta ata cac tgg cga atg cga aag aac tgc ttg cag cgt      2046
Lys Ser His Val Ile His Trp Arg Met Arg Lys Asn Cys Leu Gln Arg
            540                 545                 550 aaa ctt ttt tcc tgc ttc acg gtc aga gta aac agc aaa acg ccg          2091
Lys Leu Phe Ser Cys Phe Thr Val Arg Val Asn Ser Lys Thr Pro
            555                 560                 565 taagaccgga aagcaaaagg ttttaaagtg atgaaaggtc tattatcatc ggcatattac    2151
agatgagcca cgtactgctc gggcccgaaa aggaatcaaa tcactatgcg ctgtaaaacg    2211
ctgactgctg cag                                                       2224

<210> SEQ ID NO 13
<211> LENGTH: 567
<212> TYPE: PRT
<213> ORGANISM: Escherichia coli

<400> SEQUENCE: 13

Met Leu Ala Gln Leu Thr Ile Ser Asn Phe Ala Ile Val Arg Glu Leu
1               5                   10                  15

Glu Ile Asp Phe His Ser Gly Met Thr Val Ile Thr Gly Glu Thr Gly
            20                  25                  30

Ala Gly Lys Ser Ile Ala Ile Asp Ala Leu Gly Leu Cys Leu Gly Gly
        35                  40                  45

Arg Ala Glu Phe Asp Met Val Arg Thr Gly Cys Arg Ala Asp Leu Cys
    50                  55                  60

Ala Arg Phe Ser Leu Lys Asp Thr Pro Ala Arg Leu Arg Trp Leu Glu
65                  70                  75                  80

Glu Asn Gln Leu Glu Asp Gly His Glu Cys Leu Leu Arg Arg Val Ile
                85                  90                  95

Ser Ser Asp Gly Arg Ser Arg Gly Phe Ile Asn Gly Thr Ala Val Pro
            100                 105                 110

Leu Ser Gln Leu Arg Glu Leu Gly Gln Leu Leu Ile Gln Ile His Gly
        115                 120                 125

Gln His Ala His Gln Leu Leu Thr Lys Pro Glu His Gln Lys Phe Leu
    130                 135                 140

Leu Asp Gly Tyr Ala Asn Glu Thr Ser Leu Leu Gln Glu Met Thr Ala
145                 150                 155                 160

Arg Tyr Gln Leu Trp His Gln Ser Cys Arg Asp Leu Ala His Gln
                165                 170                 175

Gln Leu Ser Gln Glu Arg Ala Ala Arg Ala Glu Leu Leu Gln Tyr Gln
            180                 185                 190

Leu Lys Glu Leu Asn Glu Phe Asn Pro Gln Pro Gly Glu Phe Glu Gln
        195                 200                 205

Ile Asp Glu Glu Tyr Lys Arg Leu Ala Asn Ser Gly Gln Leu Leu Thr
    210                 215                 220

Thr Ser Gln Asn Ala Leu Ala Leu Met Ala Asp Gly Glu Asp Ala Asn
225                 230                 235                 240

Leu Gln Ser Gln Leu Tyr Thr Ala Lys Gln Leu Val Ser Glu Leu Ile
                245                 250                 255

Gly Met Asp Ser Lys Leu Ser Gly Val Leu Asp Met Leu Glu Glu Ala
            260                 265                 270

Thr Ile Gln Ile Ala Glu Ala Ser Asp Glu Leu Arg His Tyr Cys Asp
```

-continued

```
                275                 280                 285
Arg Leu Asp Leu Asp Pro Asn Arg Leu Phe Glu Leu Glu Gln Arg Ile
        290                 295                 300
Ser Lys Gln Ile Ser Leu Ala Arg Lys His His Val Ser Pro Glu Ala
305                 310                 315                 320
Leu Pro Gln Tyr Tyr Gln Ser Leu Leu Glu Glu Gln Gln Gln Leu Asp
                325                 330                 335
Asp Gln Ala Asp Ser Gln Glu Thr Leu Ala Leu Ala Val Thr Lys His
        340                 345                 350
His Gln Gln Ala Leu Glu Ile Ala Arg Ala Leu His Gln Gln Arg Gln
        355                 360                 365
Gln Tyr Ala Glu Glu Leu Ala Gln Leu Ile Thr Asp Ser Met His Ala
        370                 375                 380
Leu Ser Met Pro His Gly Gln Phe Thr Ile Asp Val Lys Phe Asp Glu
385                 390                 395                 400
His His Leu Gly Ala Asp Gly Ala Asp Arg Ile Glu Phe Arg Val Thr
                405                 410                 415
Thr Asn Pro Gly Gln Pro Met Gln Pro Ile Ala Lys Val Ala Ser Gly
                420                 425                 430
Gly Glu Leu Ser Arg Ile Ala Leu Ala Ile Gln Val Ile Thr Ala Arg
        435                 440                 445
Lys Met Glu Thr Pro Ala Leu Ile Phe Asp Glu Val Asp Val Gly Ile
    450                 455                 460
Ser Gly Pro Thr Ala Ala Val Val Gly Lys Leu Leu Arg Gln Leu Gly
465                 470                 475                 480
Glu Ser Thr Gln Val Met Cys Val Thr His Leu Pro Gln Val Ala Gly
                485                 490                 495
Cys Gly His Gln His Tyr Phe Val Ser Lys Glu Thr Asp Gly Ala Met
                500                 505                 510
Thr Glu Thr His Met Gln Ser Leu Asn Lys Lys Ala Arg Leu Gln Glu
        515                 520                 525
Leu Ala Arg Leu Leu Val Ala Val Lys Ser His Val Ile His Trp Arg
        530                 535                 540
Met Arg Lys Asn Cys Leu Gln Arg Lys Leu Phe Ser Cys Phe Thr Val
545                 550                 555                 560
Arg Val Asn Ser Lys Thr Pro
                565
```

RECOMBINANT NUCLEIC ACID SEQUENCES AND METHODS FOR DETERMINING BOTH GENOTOXICITY AND MUTAGENICITY OF A SAMPLE AND THE KINETICS OF THE GENOTOXICITY

This application is a Continuation of U.S. patent application Ser. No. 09/171586, filed Dec. 2, 1998, which is incorporated herein by reference.

There are at present various screening methods for genotoxic and/or toxic compounds using microorganisms. The Ames test (Maron and Ames, 1983) appears to be the most widely used test for toxic compounds and is as such recommended worldwide. It however takes about three days for completion of the test with the obvious concomitant disadvantages.

Some short term methods have been introduced wherein the SOS response caused by DNA damage is measured as an amount of β-galactosidase expressed by the lacZ gene positioned downstream of the umuD,C or sfiA stress induced promoters that are SOS regulated. These tests are known respectively as the umu test (Oda et al. 1985) using *Salmonella typhimurium* as host microorganism and SOS chromotest (Quillardat et al., 1982) using *E. coli* as host microorganism. In the umu test and SOS chromotest the host microorganism is cultured in the presence of the sample to be tested and subsequently the host microorganism is disrupted. A substrate for β-galactosidase is then added and the ensuing reaction is terminated after some 10 minutes by addition of an inhibitor followed by OD measurement at two wave lengths and calculation or β-galactosidase activity. These tests overcome the long timespan problem of the Ames test, however, have their own disadvantages. The sensitivity is low and detection times are still a lengthy 7–8 hours. In particular the detection sensitivity of nitroarenes and polycyclic aromatic hydrocarbons is low. In addition the detection method requires a large number of actions and additions of various reagents thereby rendering the method complicated and expensive. Due to the fact that the cell has to be disrupted in order to carry out detection of any induction it is only possible to carry out one measurement on the cell.

EP-A-0.649.905 discloses that some of the disadvantages of the aforementioned tests can be overcome by placing an SOS gene upstream of a gene expressing luciferase activity such that luciferase expression occurs simultaneously with expression of the SOS gene. Subsequently a mutagenic substance can be detected or measured in a short time by measuring the luminescence. Any SOS gene is stated as being useful and the umuD,C gene (as used in the umu test) is illustrated in the examples. The sensitivity of this test is stated to be increased in comparison to that of the conventional tests i.e. the SOS chromotest and the umu test because of the smaller sample volume required for detection measurement. No relevance is attached to the promoter to be used other than the fact it must be SOS inducible. As luminescence production is immediate the measurement can occur earlier than with the lac system thereby shortening the detection time.

In WO 94/13831 DuPont also disclose the use of stress inducible promoters in combination with a luminescence gene complex to provide a genetically engineered microorganism. They state "although stress responses have been demonstrated to be useful in detecting the presence of various environmental insults it has yet to be linked to a sensitive easily detected reporter". DuPont provides an extensive list of stress inducible promoters known in the state of the art that could be useful according to them but to which the invention is not restricted. This list comprises promoters from the following regulatory circuits: heat shock, SOS, hydrogen peroxide, superoxide, fatty acid starvation, universal stress, resting state, stringent, catabolite activation, P utilisation and N utilisation. In the Examples they use the heat shock regulated protein promoters dnaK and grpE, the SOS regulated promoters recA and uvrA, the oxidative damage regulated promoters katG and micF, the universal stress promoter uspA, the stationary phase promoter xthA, the his promoter from the amino acid starvation circuit, the lac promoter involved with the carbon starvation circuit, the phoA promoter from the phosphate limitation circuit and the glnA promoter from the nitrogen limitation circuit. This large number of examples from such a broad range of differently regulated promoters presumably serves to illustrate the broad applicability of their system. No preference is expressed or deducible for any particular group of promoters or any individual promoter. The only explicit reference to a specific SOS regulated promoter occurs in one of the examples (example 12 of the patent application) in which results with the SOS regulated promoter recA are presented. After exposing the microorganism to samples with the mutagen ethidium bromide at a concentration of 0.25 mg/ml an induction ratio of 1.9 was measured in one measurement after 180 minutes of the addition of mutagen. After addition of 0.5 μg/ml mitomycin C, the induction ratio's were measured after 100 minutes. Depending on the test strain used they varied between 4.7 to 20. This is apparent from Example 12 of the DuPont application.

Unexpectedly we have found a subgroup of stress induced promoters, in fact a subgroup of SOS regulated promoters which in combination with a luminescence reporter can be used in a microorganism system for assessing mutagenicity with improved results. This subgroup does not include the SOS regulated RecA promoter. This subgroup offers a number of advantages over the DuPont RecA-luciferase system and the other microbial toxicity testing sytems of the state of the art. In further testing and developing these new systems by mutating the promoters in a specific manner we were able to improve performance even more. In addition novel methods of testing were carried out. These novel methods of testing result in obtaining more and better data hitherto not described for any of the existing microbial toxicity tests.

The subject invention is directed at a recombinant nucleic acid sequence comprising an SOS regulated promoter with an induction ratio higher than 40, said promoter being operatively linked to a reporter encoding nucleic acid sequence encoding a reporter resulting in a signal that can be assayed as light production. Preferably a promoter with an even higher induction ratio, preferably higher than 50 is present in the recombinant nucleic acid sequence according to the invention. The induction ratio can e.g. be determined as disclosed by M. Schnurr et al. in Biochimie (1991) 73, 423–431. Alternatively the method disclosed by Peterson K. R. and Mount D. W. (1987), J. Mol. Biol. 193, 27–40 can be used. The disclosures are hereby incorporated by reference. The recA promoter disclosed in the state of the art in combination with luciferase does not fall within this categery as the induction ratio of recA is appreciably lower. It is 11× at 30° C. which is the incubation temperature of the test. The induction ratio is an art recognised term and can be ascertained in a manner known per se for a person skilled in the art. In the literature Examples are given of how the induction ratio can be and has been ascertained together with numerical values for a number of promoters. The low induction ratio of recA is probably the reason why it is not particularly suited for a sensitive detection system based on promoter induction. The RecA promoter is the earliest promoter to be induced in the SOS regulated system. The signal(s) generated by metabolic defect(s) is (are) sensed by RecA protein. It also purportedly has a second function in mutagenesis in assisting DNA polymerase to bypass lesions. During the first twenty minutes after DNA damage the uvrA,B,C,D genes are activated to commence with excision repair. Then the recombinatorial repair pathway known as the RecF recombination pathway is very active during approximately 40 minutes. Finally, the SOS mutagenesis pathway involving umu D,C is induced.

The lowest level of mytomycin C that was used in the dupont system as illustrated in the above cited patent application was 500 ng/ml. No indication or suggestion of detection of lower levels is given. In the subject systems 7 ng/ml of mytomycin can be detected. This system is thus approximately 80 times more sensitive than the DuPont system has been illustrated to be. We found induction ratios higher than 2 from a concentration of 7.5 ng/ml in our system.

We illustrate for the first time on line measurement. On line measurement was not possible with the SOS or Ames test because of the disruption of the cell required. The other tests described have also only been used for single point determinations. We have now discovered it is possible to distinguish the presence of multiple mutagens in a sample and to determine the induction kinetics of such substances. It was totally unexpected that the presence of multiple mutagens would provide detectably different signals when following the luminescence development in time. One would to the contrary have expected a cumulative effect to arise. It is however clearly illustrated that the SOS regulated promoters form a group of promoters that exhibit such characteristics of regulation that the induction pattern differs sufficiently for various inducing chemicals to present differentiated detectable signals. The novel method is extremely simple to apply and the detection of signal can be automated. The novel method merely requires culturing a microorganism comprising an SOS regulated promoter, said promoter being operatively linked to a reporter encoding nucleic acid sequence, said reporter resulting in a signal that can be assayed as light production and contacting the microorganism with the sample to be tested followed by measuring the luminescence of the culture, said measuring occurring at various points in time and determining the signal to noise ratio at said points in time, plotting the data, said data representing the kinetics of genotoxicity of said sample with multiple peaks being indicative of multiple genotoxicity compounds with different induction kinetics. Preferably the luminescence measurements are continuous. Preferably the method is carried out on line. The examples and concomitant figures illustrate the fact that various peaks are detectable with samples comprising multiple mutagens.

In a preferred embodiment the luminescence determination occurs continuously. This is particularly interesting from the point of view of automation as well as accuracy of determination of the presence of multiple genotoxic agents. The higher the signal to noise ratio the more sensitive the testing system is. Other factors that are of interest are the speed of induction, the degree of expression and the degree of fluctuation in signal to noise ratio. These factors can vary depending not only on the selected promoter but also on the host strain and the nature of the genotoxic agents. For practical uses the signal to noise ratio will be equal to or higher than 2 for 2 concentrations of genotoxic compound. A person skilled in the art will select the system best suited to their situation on the basis of one or a number of the aforementioned characteristics. The following examples illustrate the broad applicability of the novel biosensor systems. Results are shown of a number of the novel biosensor systems according to the invention consisting of various embodiments of the novel DNA sequences according to the invention in *E. coli* and in *S. typhimurium* strains. All the novel biosystems tested were better than the standard Ames and SOS chromotests which ar based on *S. typhimurium* and *E. coli* strains. The systems according to the invention were faster, more acccurate and more sensitive. We illustrate clearly for agents known to provide false negative results in the SOS chromotest and the Ames test that the novel systems according to the invention provide positive results where the known tests indeed provide false negative results. Specifically this is illustrated for novobiocine, sodiumazide, mitomycin C, naladixic acid, hydrogen peroxide, pyrene and phenantrene. The test systems according to the invention are particularly suited for detecting the presence of PAH's (=polyaromatic hydrocrbons).

In addition the systems according to the invention do not require disruption in order to provide a measurement which is why they can subsequently be used for further testing and more importantly can provide a detectable signal over a period of time. Thus the induction kinetics of samples can be followed and determined.

An important embodiment of the invention lies in the fact that now for the first time a method for determining the presence of multiple genotoxic compounds in a sample has become available, said method comprising the steps of culturing a host microorganism, said host microorganism comprising a nucleic acid sequence comprising an SOS regulated promoter, said promoter being operatively linked to a reporter encoding nucleic acid sequence encoding a reporter resulting in a signal that can be assayed as light production, measuring the luminescence of the culture, said measuring occurring at various points in time, preferably continuously and determining the signal to noise ratio at said points in time, plotting the data, said data representing the kinetics of genotoxicity of said sample with multiple peaks being indicative of multiple genotoxicity compounds with different induction kinetics.

Due to selection of the novel DNA sequences and employment thereof in host cells rendering novel biosensor systems we have also created very sensitive and fast biosystems. The genoxicity of a sample can be ascertained within a time period of 5 minutes to two hours.

Another embodiment of the invention thus comprises a method for determining the presence of a genotoxic compound in a sample, said method comprising the steps of culturing a host microorganism, said host microorganism comprising a nucleic acid sequence comprising an SOS regulated promoter with an induction ratio higher than 20, said promoter being operatively linked to a reporter encoding nucleic acid sequence encoding a reporter resulting in a signal that can be assayed as light production.

measuring the luminescence of the culture at multiple point in time and determining whether the luminescence of the culture has changed, increased luminescence being indicative of the presence of a genotoxic compound. Preferably the induction ratio of the promoter will be 40 or more, suitably 50 or more. In the aforementioned method for determining the presence of a genotoxic compound in a sample, a preferred embodiment comprises measuring of luminescence at multiple points in time. Preferably the measurements are carried out continuously. Preferably in addition the steps of determining the signal to noise ratio of luminescence at said points in time and plotting the luminescence signal to noise data, said plot representing the kinetics of genotoxicity or said sample for determining the kinetics of genotoxicity of a sample. The aforementioned methods are preferably carried out with the biosensors according to the invention. Such biosensors comprise a host strain comprising the novel nucleic acid sequence according to the invention as defined elsewhere in this description. Preferably the host strain is a microorganism such as an *E. coli* or *S. typhimurium* strain. In particular the standard *S. typhimurium* Ames test strains have been applied as host strains and provide very suitable embodiments of a biosensor according to the invention. Strains according to the invention offer the attraction of being suited for both genotoxicity and toxicity testing. Examples of Ames test strains are TA98, TA100, TA102, TA104, TA1535 and TA1538 or the new *S. typhimurium* strains TA7001 to TA7006 and TA7046 (Gee et al., 1994). Also the Ames strains are standard strains that are acceptable world wide in the pharmaceutical industry. In the case of the biosensor according to the invention comprising an Ames strain as host cell the strain cannot only be used for genotoxicity testing according to the invention but also subsequently for the Ames test as such. Other suitable host strains that can thus become multifunctional will be obvious to a person skilled in the art.

Various embodiments of the nucleic acid sequence according to the invention suitable for application in a biosensor according to the invention are illustrated in the examples. A nucleic acid sequence comprising an SOS regulated promoter with an induction ratio higher than 40, said promoter being operatively linked to a reporter encoding nucleic acid sequence encoding a reporter resulting in a signal that can be assayed as light production is part of the invention. Biosensors according to the invention comprise such a nucleic acid sequence in any of the various embodiments disclosed herein. Such a DNA sequence is furthermore suitable for carrying out all the methods according to the invention as disclosed herein.

Suitable promoters from the recombinatorial repair promoters consist of the group RecF, RecJ, RecN, RecO, RecQ, ruv and uvrD promoters. The RecN promoter is illustrated in the examples. Another suitable promoter is the SfiA promoter which is also illustrated in the examples. In addition mutated promoters of the aforementioned group of SOS regulated promoters induced during recombinatorial repair having an induction ratio higher than 40 are also suitable embodiments. Such mutants may have increased promoter strength or regulation but it is vital the SOS regulation is not destroyed. An example of an extremely suitable mutation comprises a mutation in at least one LexA binding site, whereby at least one other LexA binding site remains active. A preferred mutation of this type will have a mutation in the at least one other LexA binding site that does not alter the wild type promoter sequence. An example of this type of mutant is the RecN mutant with sequence id no 9 (RecN1-3).

The type of mutant with LexA mutation is particularly useful in the method of determining presence of multiple genotoxic agents and determining induction kinetics of such samples in the methods according to the invention as disclosed elsewhere in the description. Such mutants are also extremely sensitive and fast. They are particularly useful for determining the appearance and/or accumulation of genotoxic intermediate degradation or metabolic products. This can be in the field of pollutants and degradation thereof for example bioremediation of soil. This can also be useful in drug testing.

Another type of mutant that has been found to provide useful characteristics is a mutation comprising a promoter up mutation. A promoter up mutation is an art recognised term, wherein the mutation is such that the promoter sequence more closely resembles that of the consensus sequence for the RNA polymerase binding site. Such a type of mutation can comprise a mutation in the promoter −35 region. An example for the RecN promoter of this type of mutation is provided in the examples in the form of RecN 2-4 mutant with sequence id. no. 10. We also provide an example of a combined mutant with both LexA and promoter up mutations in the form of the RecN 3-4 mutant with the sequence id no 11. In promoter region and better spacing between the −35 and −10 region. These latter two options were not relevant for recN as this promoter already exhibits good correspondence to the $\sigma^{35}$ promoter sequence. As the −35 was not optimal we illustrated that a mutation rendering a closer correspondence to the a $\sigma^{35}$ promoter sequence resulted in an improvement.

In addition to the promoter sequence the nucleic acid sequence according to the invention also comprises a reporter encoding nucleic acid sequence encoding a reporter resulting in a signal that can be assayed as light production. Such sequences are known in the state of the art. A suitable embodiment if formed by a reporter encoding nucleic acid sequence comprising a luciferase A and B genes. In a preferred embodiment the sequence further comprises the luciferase C, D and E genes required for producing the limiting fatty acids substrate that is used in recycling. Details of such sequences can be found in WO92/15687 with filing date Feb. 2, 1992.

A preferred method according to the invention comprises applying a microorganism suitable as Ames test strain, said microorganism further comprising a novel nucleic acid sequence according to the invention in any of the methods according to the invention described herein followed by a classical Ames test, thereby providing a method of genotoxicity mutagenicity and toxicity testing using the same strain.

Another application of the novel nucleic acid sequences according to the invention lies in use of a host microorgaanism comprising said sequence for determining toxicity. A preferred host cell is one capable of a high noise signal. For example nucleic acid sequences according to the invention with promoterup mutation as described above appear very suitable for this application. Such application can lead to IC50 calculation of toxic products. In other words a method for determining the presence of a toxic compound in a sample, said method comprising the steps of culturing a host microorganism, said host microorganism being a host microorganism according to the invention as disclosed in any of the embodiments herein, measuring the luminescence of the culture and determining whether the luminescence of the culture has changed, decreased luminescence being indicative of the presence of a toxic compound is comprised within the scope of the invention.

In summary the following advantages of the invention can be given:

- The possibility is created of discerning the presence of at least two genotoxic compounds presenting different induction kinetics in a sample.
- The possibility is created of identifying in time the formation of intermediate genotoxic products during their metabolisation with S9 for example or degradation e.g. in bioremediation.
- Kinetics of genotoxicity as well as general toxicity can be detected on line with the same cells.
- A rapid test with a clear answer can be provided within a time of 5 minutes to 4 hours, preferably within 3 hours, more preferably within 2 hours.
- No preliminary treatment of the cell culture prior to signal detection is required.
- No disruption of the cells is required for on line detection of genotoxic compounds or general toxicity of a liquid solution.
- Selected substances found to be genotoxic within 4 hours, preferably within 3 hours, more preferably within 2 hours can be further examined with the strains according to the invention for frame shift mutations or base pair substitutions with the same cells according to the Ames procedure.
- There is no need for internal controls for toxicity because the decrease in basic light production is indicatoive of general toxicity.
- Due to the limited test time of the experiment no strict sterile conditions are needed.
- Due to the limited test time of the experiment no chemical stability tests for the test sample are needed.

FIGURE DESCRIPTION

FIGS. 1a and 1b: restriction maps of promoter probe vector pMOL877 (FIG. 1a) and its derivative pMOL890 (FIG. 1b) in which the sfiA promoter is cloned.

FIGS. 2a–2d: restriction maps of the promoter probe vector pMOL877 derivatives pMOL1066 (FIG. 2a), pMOL1067 (FIG. 2b), pMOL1068 (FIG. 2c) and pMOL1069 (FIG. 2d) in which the recN promoter (pMOL1066, recN1-2), a recN promoter with an inactivated LexA2 site (pMOL1067, recN1-3), a recN promoter with a promoter up mutation (pMOL1068, recN2-4) and a recN promoter with both the promoter up mutation and the inactivated LexA2 site (pMOL1069, recN3-4) are cloned.

FIG. 3: light induction kinetics presented as signal/noise ratio of E. coli ED8739 containing pMOL890, pMOL1066, pMOL1067, pMOL1068 or pMOL1069 challenged with 64 ppm MMS. The light production was measured during 2 hours.

Figure 4:
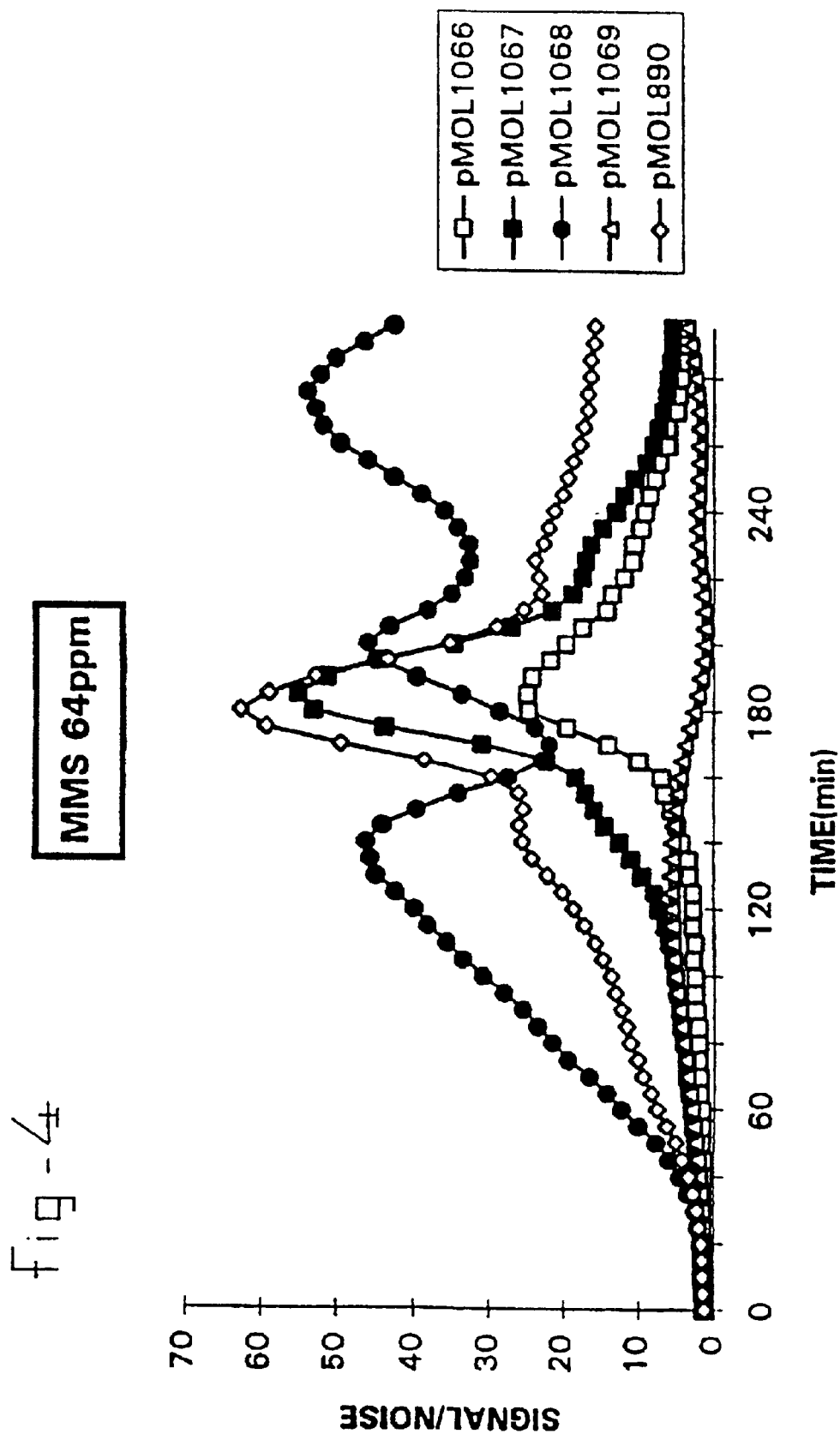

FIG. 4: light induction kinetics presented as signal/noise ratio of E. coli ED8739 containing pMOL890, pMOL1066, pMOL1067, pMOL1068 or pMOL1069 challenged with 64 ppm MMS. The light production was measured during 5 hours.

Figure 5:
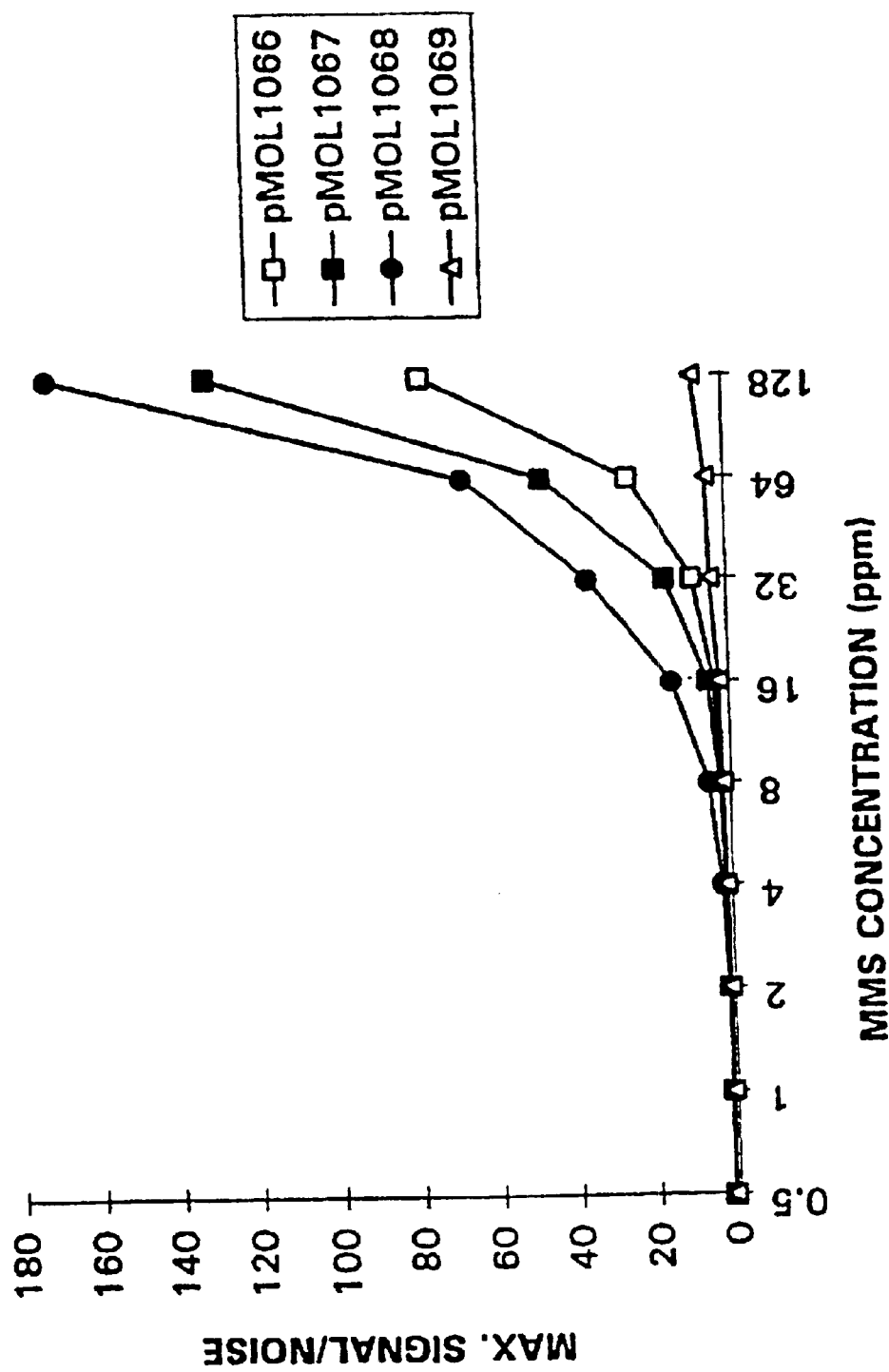

FIG. 5: dose effect curves for MMS (concentrations from 0.5 to 128 ppm) presented as maximum signal/noise ratio against concentration for E. coli ED8739 containing pMOL1066, pMOL1067, pMOL1068 or pMOL1069.

Figure 6:
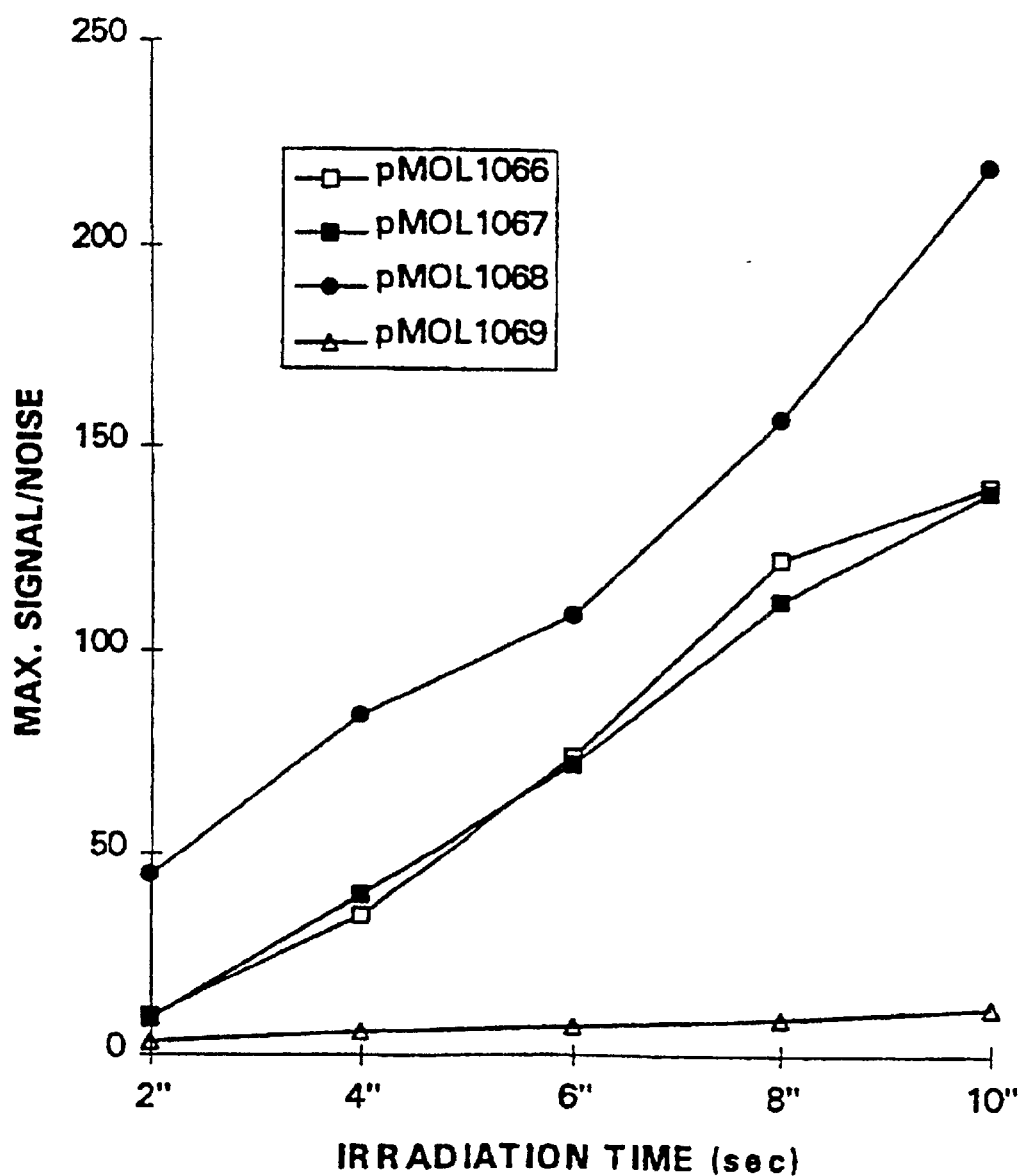

FIG. 6: dose effect curves for U.V. (irradiation time from 2 to 10 sec.) presented as maximal signal/noise ratio against irradiation time for E. ED87391106 containing pMOL1066, pMOL1067, pMOL1068 or pMOL1069.

Figure 7:
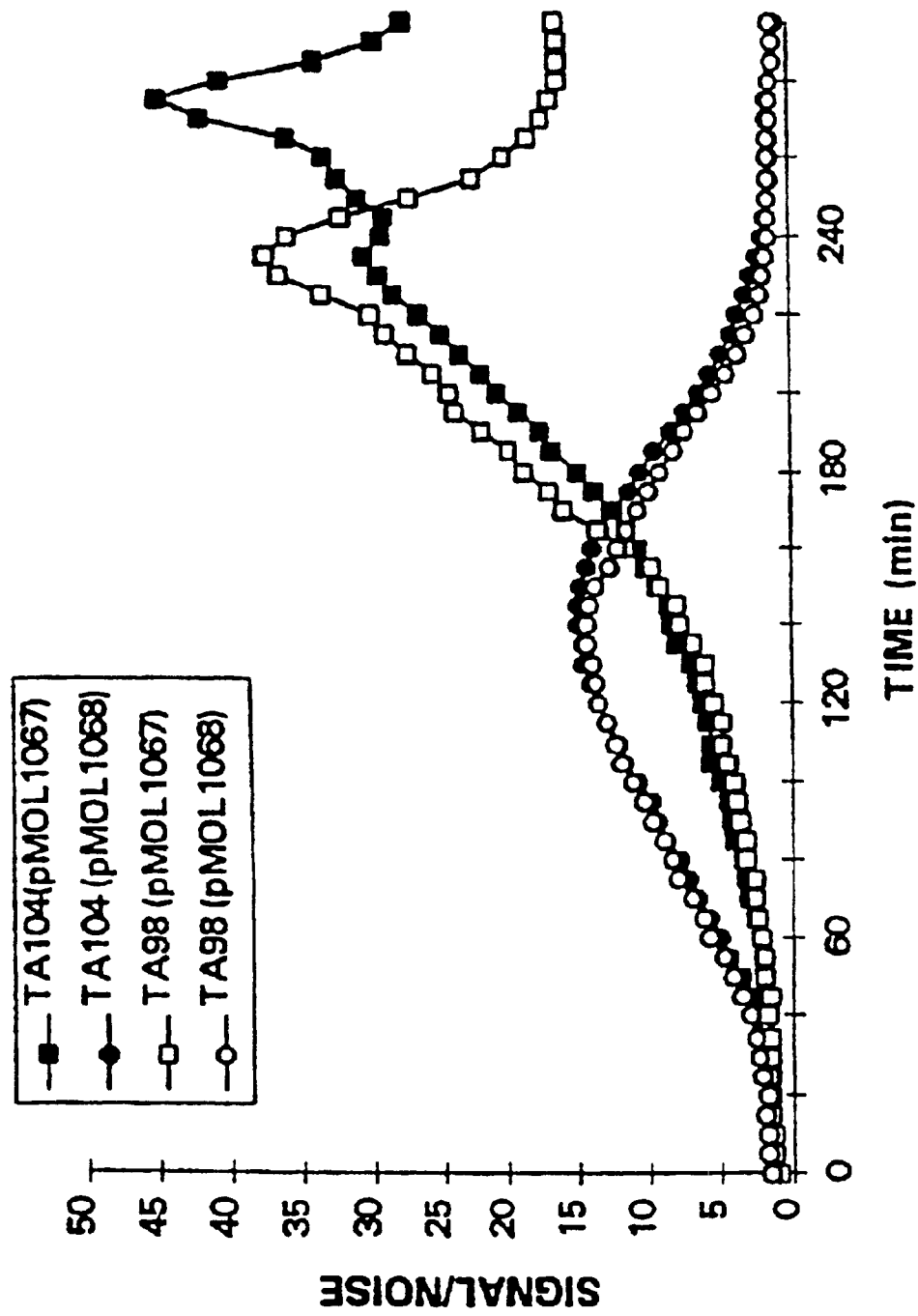

FIG. 7: light induction kinetics presented as signal/noise ratio of S. typhimurium TA98 and TA104 containing pMOL1067 or pMOL1068 challenged with 64 ppm MMS. The light production was measured during 5 hours.

Figure 8:
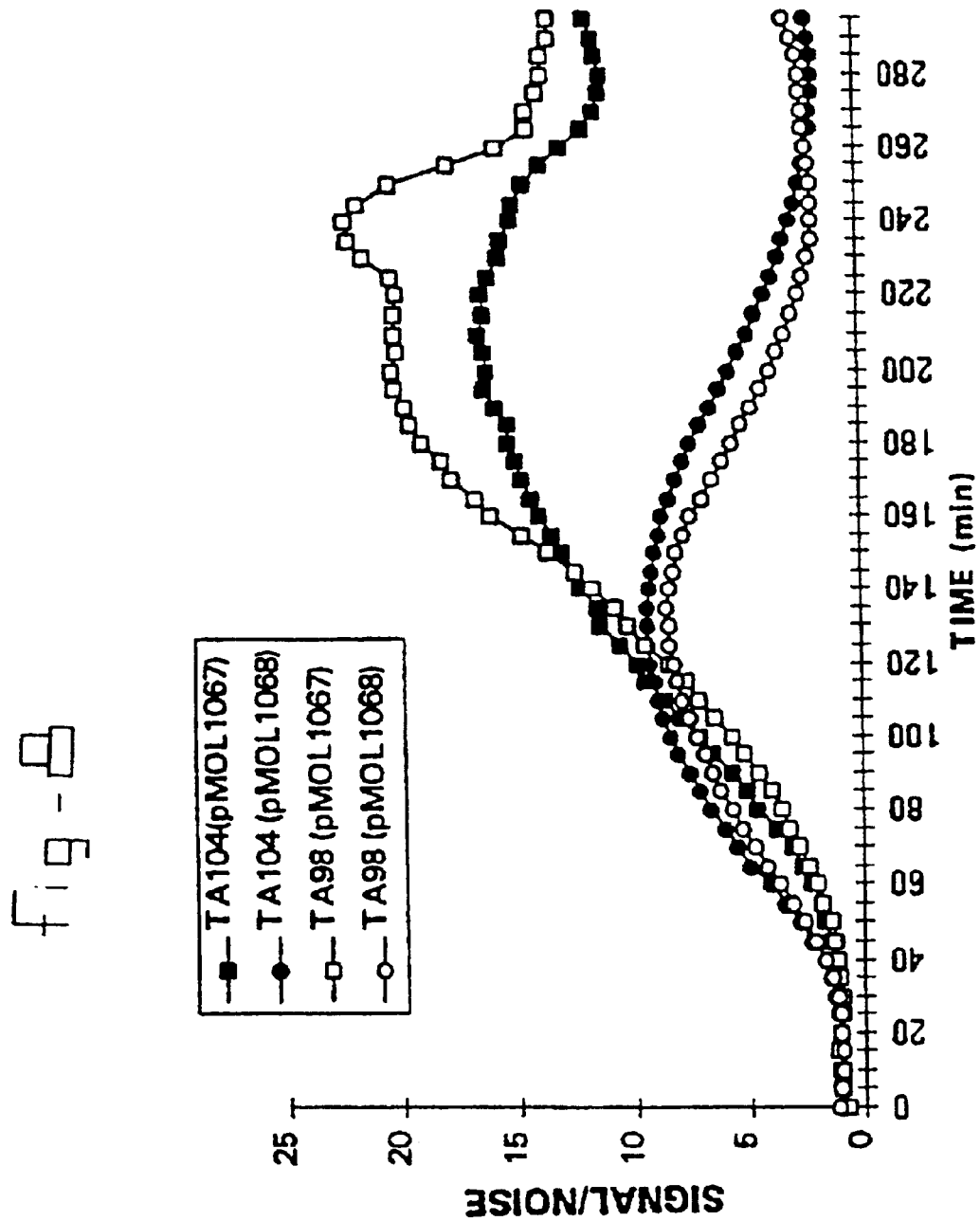

FIG. 8: light induction kinetics presented as signal/noise ratio of S. typhimurium TA98 and TA104 containing pMOL1067 or pMOL1068 challenged with 25.6 ppb 4-NQO. The light production was measured during 5 hours.

Figure 9:
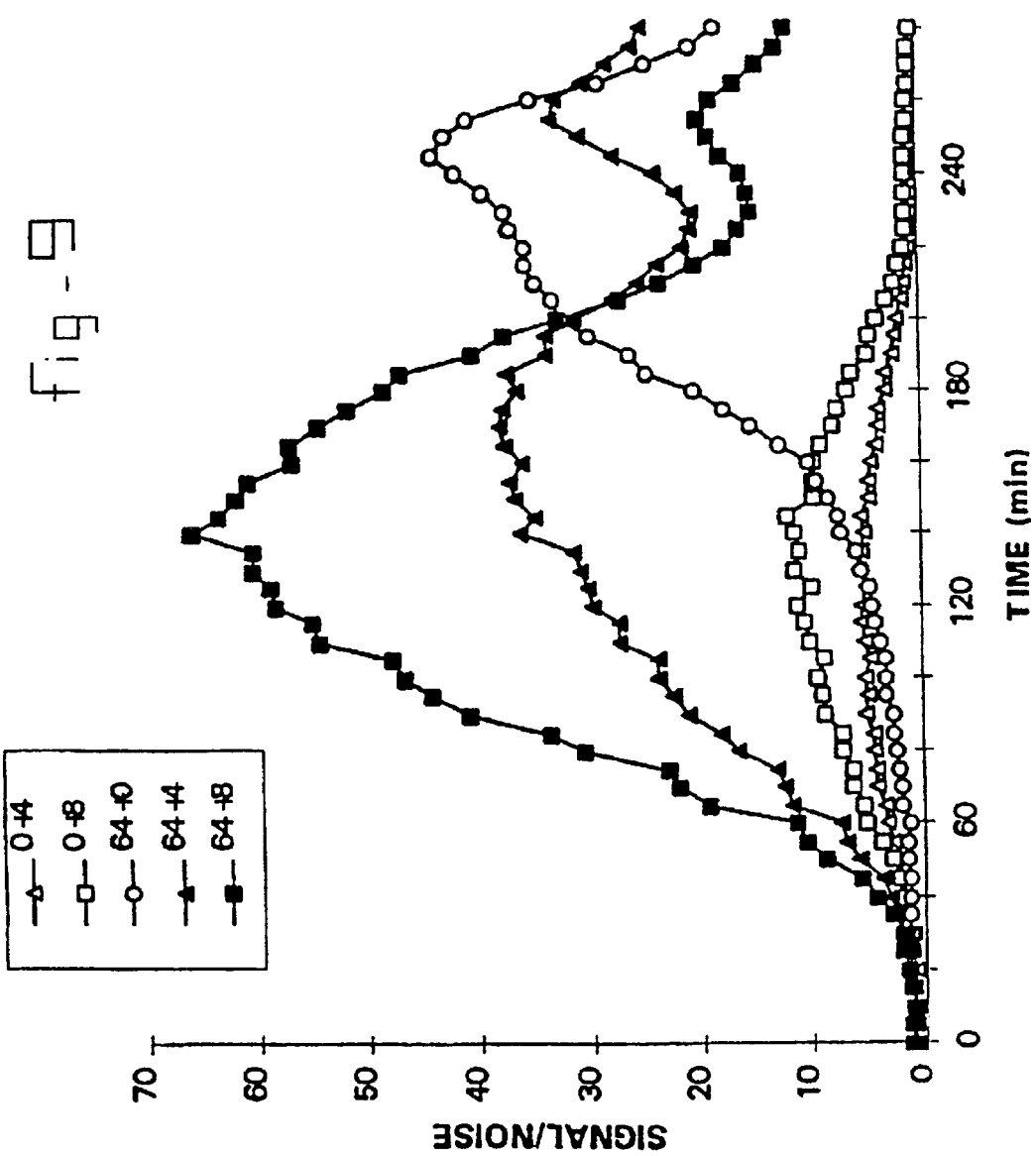

FIG. 9: testing of combinations of MMS and novobiocine with TA98 (pMOL1067). Light induction kinetics were presented as signal/noise ratio. In the legend, the first value represents the amount of MMS (in ppm) followed by the value for novobiocine (in ppm).

Figure 10:
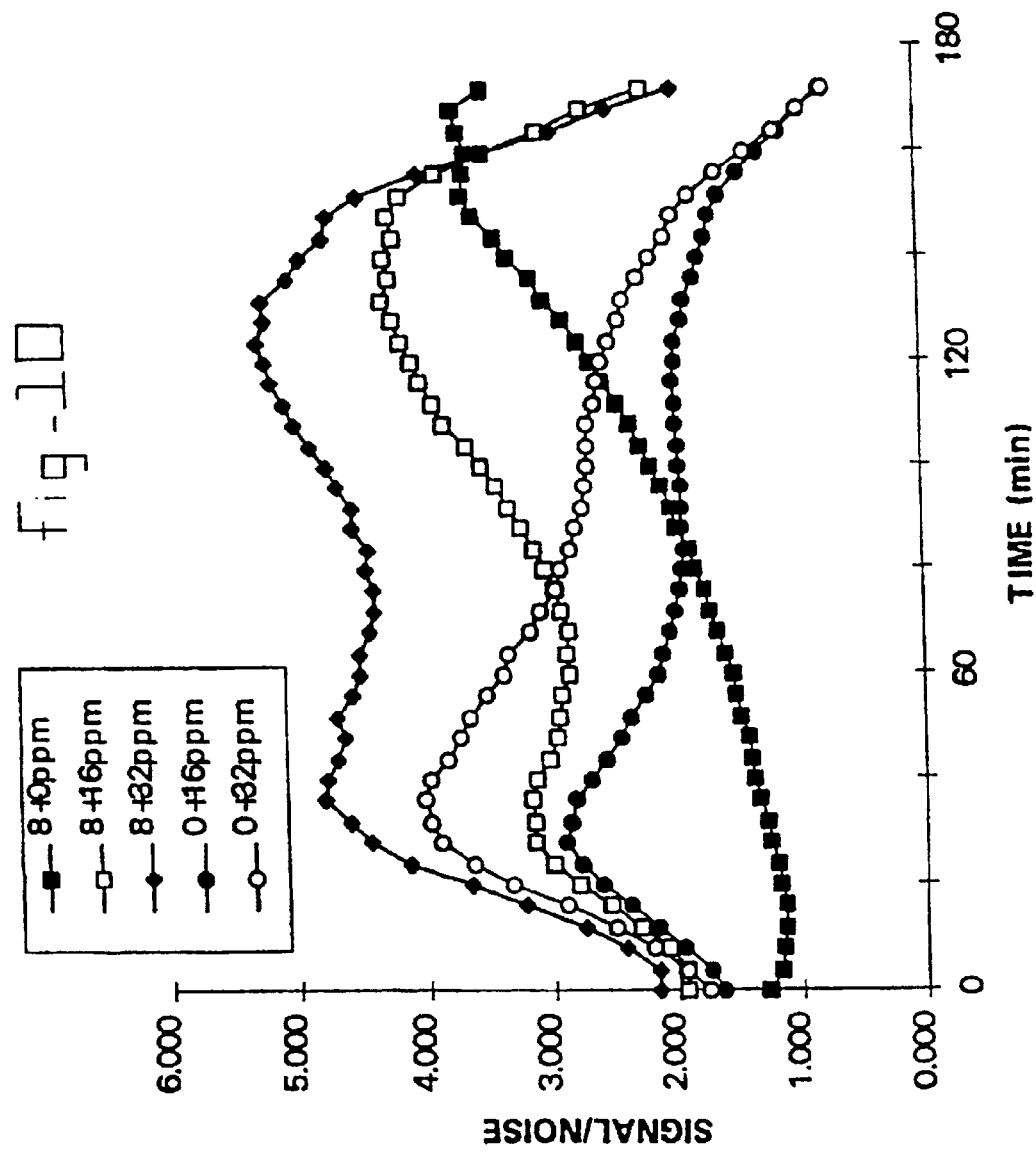

FIG. 10: testing of combinations of MMS and novobiocine with TA104 (pMOL890). In the legend, the first value represents the amount of MMS (in ppm) followed by the value for novobiocine (in ppm).

Figure 11:
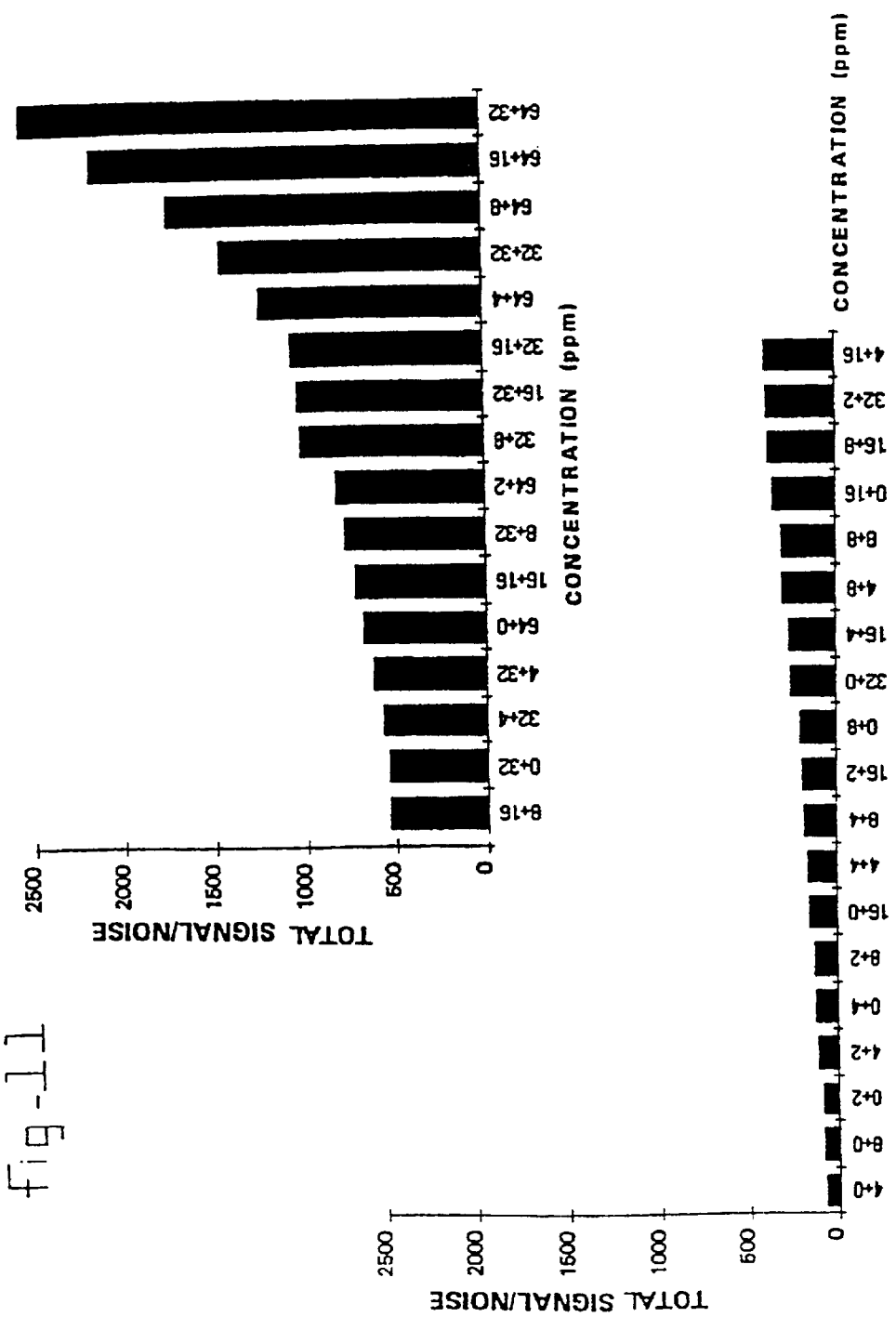

FIG. 11: genotoxicity ranking of combinations of MMS and novobiocine in function of the total signal/noise ratio as obtained with the strain TA98 (pMOL1067).

Figure 12:

FIG. 12: genotoxicity ranking of combinations of MMS and novobiocine in function of the total signal/noise ratio as obtained with the strain TA104 (pMOL890).

Figure 13:
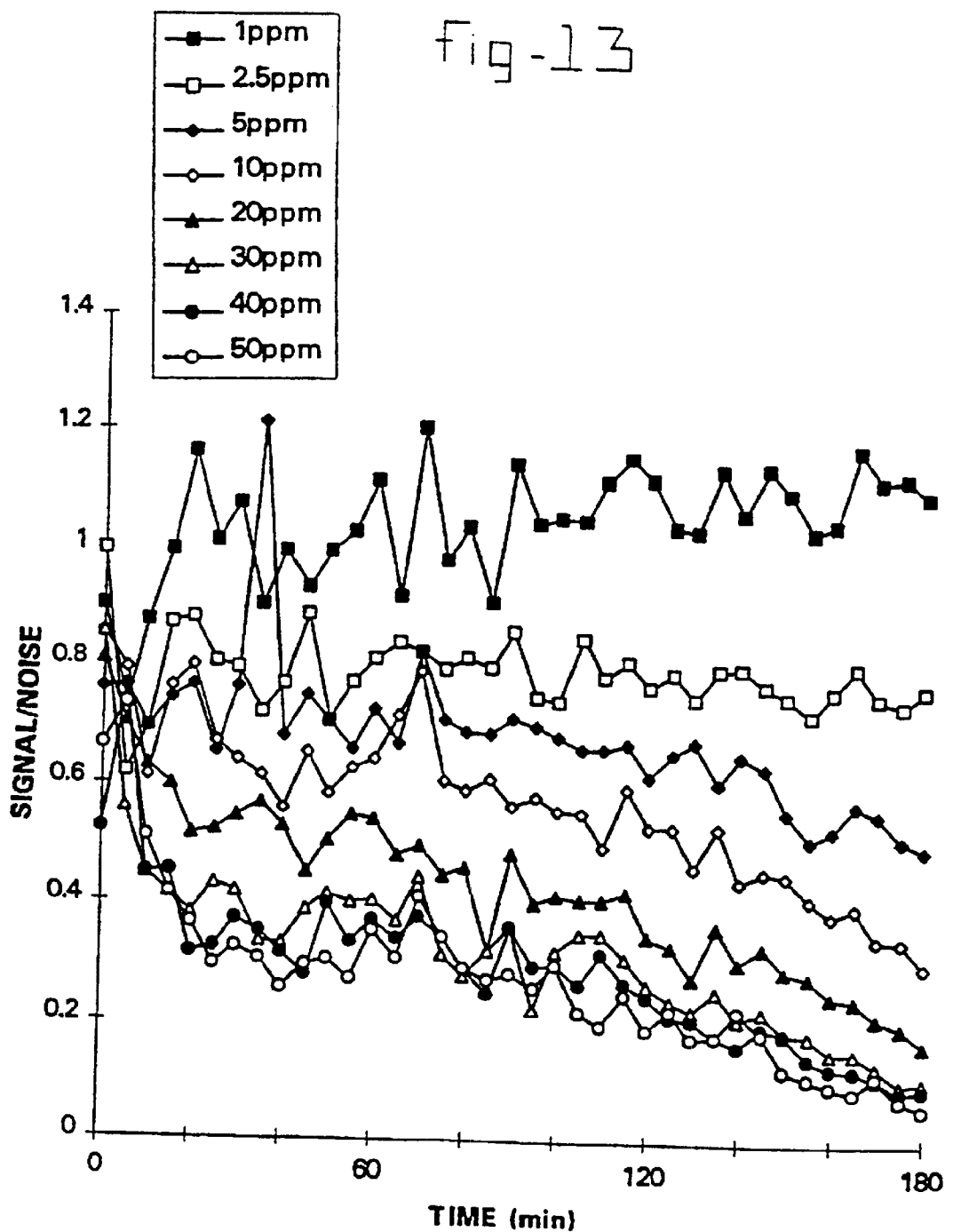

FIG. 13: decrease in time of the signal/noise ratio found for TA98 (pMOL1067) when the strain is incubated with different concentrations of the toxic product R116.

Figure 14:
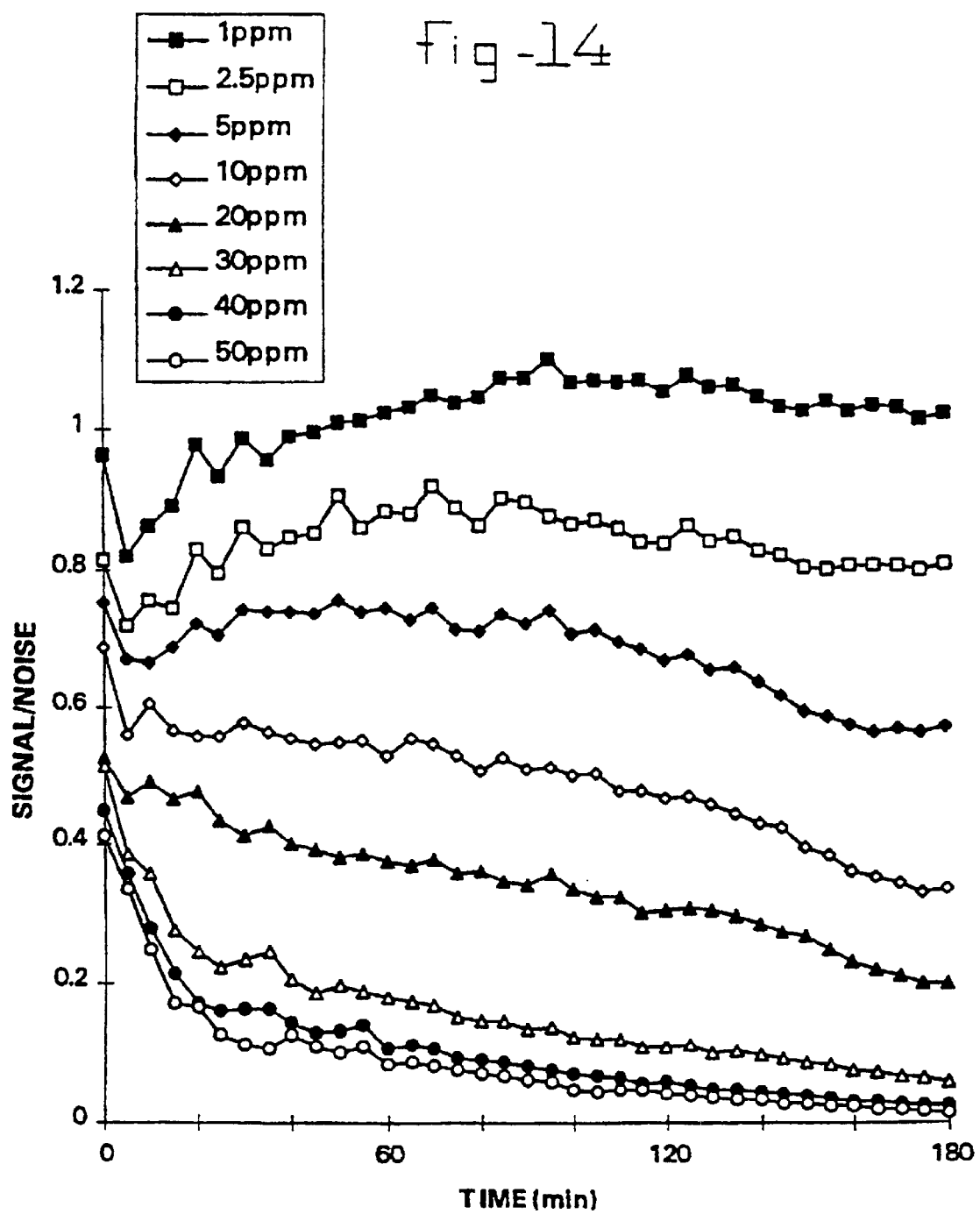

FIG. 14: decrease in time of the signal/noise ratio found for TA98 (pMOL1068) when the strains were incubated with different concentrations of the toxic product R116.

Figure 15:
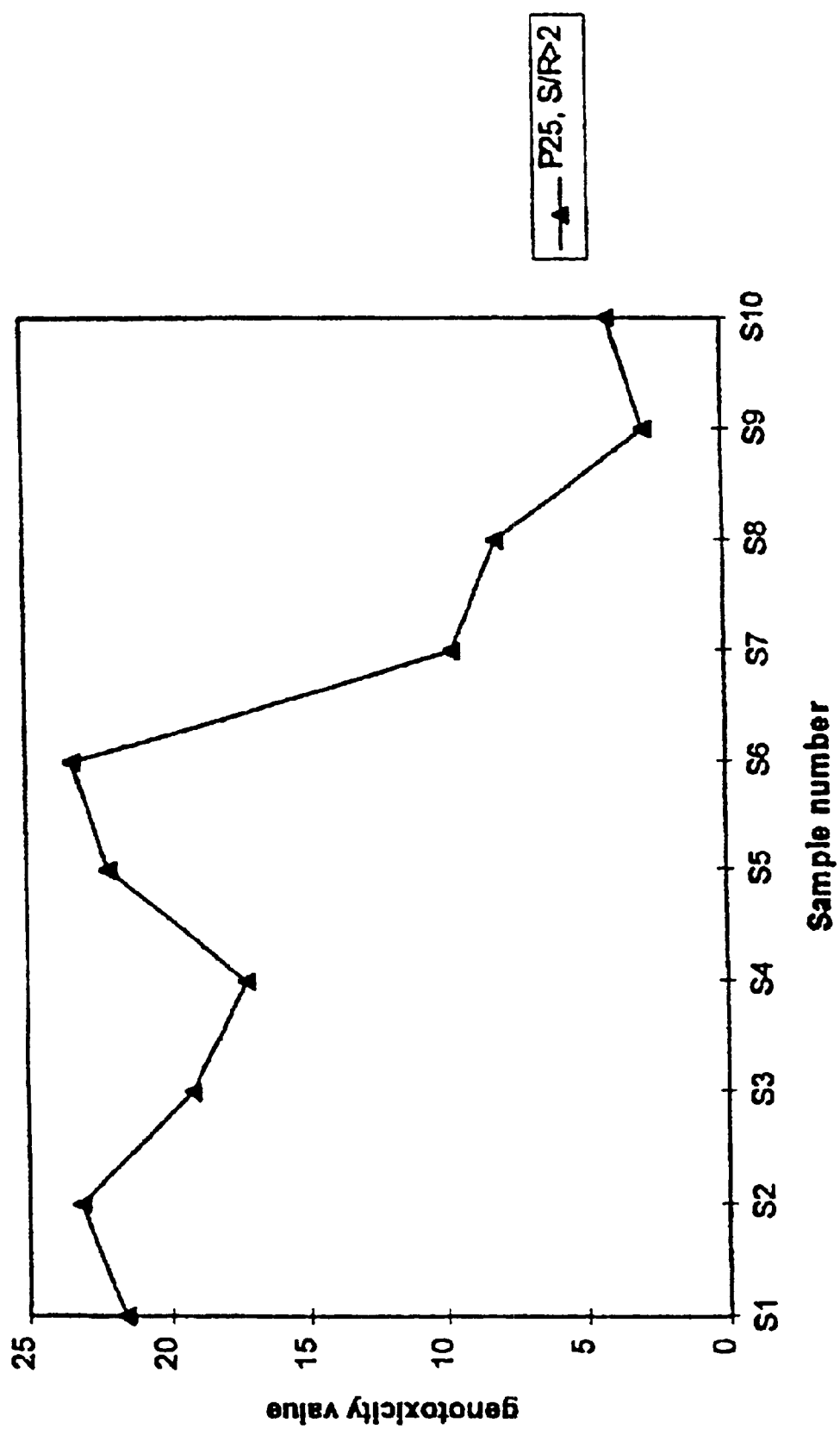

FIG. 15: genotoxicity values of samples taken during the bioremediation process of soil polluted with PAH's. The data for this experiment were obtained using TA104 (pMOL890). Genotoxicity was measured after metabolic activation with S9 extract. Similar data were obtained using TA104 (pMOL 1067) or TA104 (pMOL 1068).

FIG. 16: appearance of genotoxic degradation intermediates during the degradation of fluoranthene by strain LB208. The data for this experiment were obtained using TA104 (pMOL890), but simular results were obtained using TA104/pMOL1067) or TA104 (pMOL1068). Increase in genotoxicity indicates the formation of genotoxic intermediate degradation products. Genotoxicity was determined as the maximal S/N ratio. Genotoxic intermediates were extracted at pH 2.5. Genotoxicity was determined without or with (#) S9 metabolic activation.

EXPERIMENTAL DATA

Construction of Promoter-lux Fusions

The sfiA promoter of Escherichia coli: construction of sfiA-lux fusion

The bacterial SOS response is under control of a number of regulatory proteins, from which the RecA protein (protease) and the LexA repressor are the most important. The presence of genotoxic products results in DNA damage. This will activate a DNA repair system, and part of this activation is the change from the inactive RecA protein to an active protease. This RecA protease has high affinity for the LexA repressor, that will become inactivated due to the proteolytic action of RecA. Inactivation of LexA followed by dissociation with its binding sites of LexA regulated promoters will result in activation of the promoters and transcription of their corresponding genes. One of the promoters under control of LexA is the sfiA promoter. The sfiA promoter has one LexA binding site that overlaps with the −10 region and the transcription start point of this promoter, and transcription activation requires the dissociation of LexA. It is also known that the sfiA promoter is one of the strongest promoters under control of the bacterial SOS response with an induction ratio of 100. The sfiA promoter was cloned as a PCR fragment. Primers were designed on the published sfiA sequence in such a manner that the PCR fragment would be flanked by a HindIII and an EcoR I restriction site. (Beck and Bremer 1980)

Primer 94C97 (Sequence id. no. 1) recognises the sfiA sequence from pos. 59 to 87: TTT AAGCTTCCCGTCACCAACGACAAAATTTGCGAGGC The HindIII restriction site is underlined, while the sfiA sequence is in italics.

Primer 94C96 (sequence id. no. 2) recognises the complementary sfiA sequence from pos. 400 to 376: AA GAATTCCCGACTCAGTTTTTGTTGCGG The EcoR I restriction site is underlined, while the complementary sfiA sequence is in italics.

PCR amplification on *E. coli* HB101 chromosomal DNA resulted in a blunt PCR fragment of 352 bp. This fragment was cloned in the unique EcoR I site of pMOL877. Plasmid pMOL877 is based on the IncQ plasmid RSF1010 and contains in addition to a tetracycline resistance marker a promoterless luxCDABE operon. Upstream of this operon a unique EcoRI site is located. After EcoR I digestion the sticky ends of the EcoR I site were made blunt using Klenow DNA polymerase. After ligation the mixture was transformed to electrocompetent cells of *E. coli* ED8739 (Murray et al. 1977). Transformants were selected for growth on tetracycline, toothpicked in duplo onto rich medium containing tetracycline, and subsequently one plate was irradiated with U.V. Positive clones that showed U.V. inducible light production were visualised using autoradiography. The plasmid content of 4 positive clones was analyzed (restriction analysis and PCR) and all were shown to contain the same recombinant plasmid. This pMOL877 based derivative that contains the luxCDABE genes under transcription control of the sfiA promoter was designated pMOL890. The restriction maps of pMOL877 and pMOL890 are presented in FIGS. 1*a* and 1*b* respectively.

As a suitable alternative for the sfiA promoter, other promoter sequences that are under control of LexA and are activated during the SOS response can be cloned upstream of the lux reporter system. This could result in new constructs that show genotoxicity as a function of light production. In particular SOS-promoters with an induction ratio higher than 40 were considered to be of interest. SOS-promoters not involved in SOS mutagenesis but those involved in part of the RecF recombinations repair pathway were considered of interest. This group comprises recF. recJ, recN, recO, recQ, ruv and uvrD (formerly recL). The SOS mutagenesis promoters RecA and umu were not considered of interest in view of their low induction ratios of 11 and 28. After a literature study, the following candidate promoter sequences were selected for further study:

The recN promoter of *Escherichia coli;*
The ruv promoter of *Escherichia coli;*
The muc promoter of the *Escherichia coli* plasmid pHM101.

From these candidates the recN promoter was chosen for further experimental work because RecN is the major constituent of the cell after induction of the SOS response and is known for its tight regulation by LexA (Finch et al. 1985; Picksly et al. 1985).

The recN Promoter of *Escherichia coli:* Construction of recN-lux Fusions

The recN promoter has three LexA binding sites, one that overlaps with the −35 region and another that overlaps with the −10 region and the transcription start point of this promoter. The third LexA binding site is postulated to be located within the coding region. In this it differs from the sfiA promoter that has only one LexA binding site. The recN promoter has the following sequence (sequence id. no. 3, Rostas, et al. (1987)). in which the positions of the −35 and −10 regions (italics) as well as the positions of the two LexA binding sites (underlined) are indicated:

```
GCCTCTTTACTTGTATATAAAACCAGTTTATACTGTACACAATAACAGTAA
     -35      LexA1          -10     LexA2
```

The promoter has similarity with the consensus promoter sequence (sequence id. no. 4) "TTGACA-16/17bp-TATAAT", but the important G of the −35 region is replaced by a T. Therefore, the expression of the recN promoter under induced conditions might be rather weak as compared to the sfiA promoter that has the sequence TTGATC for its −35 region.

Based on this information the following cloning experiments were carried out:

Cloning the wild type recN promoter by PCR amplification. Two primers, primer 1 sequence id. no. 5 upstream and primer 2 sequence id. no. 6 downstream of the promoter region, were synthesised that both introduce an EcoRI restriction site. Primer 1 is located at position 28–49 of the recN sequence. Primer 2 is located at position 550–526 of the recN sequence (complementary). GAATTC in the primers indicates an EcoRI site. The recN sequence is disclosed by Rostas et al. (1987). These restriction sites are required to clone the promoter fragment in the pMOL877 lux reporter vector.

Eliminating the LexA2 binding site from the promoter sequence. For this purpose a primer 3 was chosen with the sequence id. no. 7 AAAGAA TTCTTATTGTGTACAGTATAAACTGG, that modifies the sequence at the last three base pairs of the LexA2 binding site. These three base pairs form a consensus and are conserved in all Lex binding sites from *E. coli* and *Salmonella typhimurium.* The base pairs in italics at the 5' end of primer 3 don't fit the wild type DNA sequence and were chosen to introduce an EcoRI restriction site. This primer must be used in combination with primer 1 for PCR amplification of the recN promoter. Primer 3 is complementary to the recN sequence at positions 360–338 (Rostas et al. 1987)

Introducing a "promoter up" mutation using primer 4 with sequence id. no. 8 (position 294–331 on recN according to Rostas et al. 1987) AAAAGAATTCTAATTT-TACGCCAGCCTCTTGACTGTAT. This primer introduces a G (bold) at the consensus position of the −35 region, and also introduces an EcoRI restriction site at the 5' end of the promoter region. To do so, the base pairs in italics at the 5' end of primer 4 don't fit the wild type DNA sequence. This primer must be used in combination with primer 2 for PCR amplification of the recN promoter.

Eliminating the LexA2 binding site from the promoter sequence and introducing a "promoter up" mutation. This can be done using the combination of primers 3 and 4 for PCR amplification of the recN promoter.

The promoter region of the recN gene was amplified using the sets of primers described above. The extra mutations were also introduced. This resulted in the following PCR fragments:

recN1-2, wild type recN promoter (=sequence id. no. 3)
recN1-3. recN promoter lacking the LexA2 site (=sequence id. no. 9)
recN2-4, recN promoter with promoter up mutation (=sequence id. no. 10)
recN3-4. recN promoter with promoter up mutation lacking the LexA2 site (=sequence id. no. 11).

These PCR fragments were all digested with EcoRI and cloned in EcoRI linearized pMOL877, a lux CDABE expression vector. The ligation mixtures were transformed to *E.coli* ED8739 (Met⁻, RecA⁺). The RecA⁺ phenotype is required to obtain SOS induced expression of the promoter-lux fusions. Transformants containing the required promoter-lux fusions were identified by induction of light emission using UV irradiation as described before for the sfiA-lux fusion. For each promoter construct, positive clones showing UV induced light emission were identified. This resulted in the following plasmids and *E. coli* strains:

pMOL1066 in strain CM2081. containing the recN1-2 lux fusion (wild type recN promoter).
pMOL1067 in strain CM2082, containing the recN1-3 lux fusion (recN promoter lacking the LexA2 site).
pMOL1068 in strain CM2083, containing the recN2-4 lux fusion (recN promoter with promoter up mutation).
pMOL1069 in strain CM2084, containing the recN3-4 lux fusion (recN promoter with promoter up mutation lacking the LexA2 site).

The restriction maps or the recN-lux fusion plasmids pMOL1066 to pMOL1069 are presented in FIGS. 2a–d.

Luminescence testing in *Escherichia coli* using the promoter-lux constructs.

To examine the inducibility of the different promoter constructs by the bacterial SOS system, induction experiments were performed using 64 ppm of MMS, this according to the protocol provided further on. As control, non-induced cells were taken. The results as signal/noise ratio are presented in FIGS. 3 and 4.

From the results it can be concluded that:

pMOL890 (sfiA), containing the wild type sfiA promoter, is very well induced and expressed after SOS induction (FIG. 3 and FIG. 4). In addition, the induction profile is very similar to the one observed with the recN-lux fusions pMOL1066 (recN1-2) and pMOL1067 (recN1-3) (see FIG. 4).

pMOL1066 (recN1-2), containing the wild type recN promoter, is less well expressed after SOS induction than its derivatives (also regarding total light production) (FIG. 3 and FIG. 4). The induction profile is very similar to the one observed with the sfiA-lux fusions pMOL890 and pMOL1067 (recN1-3) (see FIG. 4).

recN1-3. containing the recN promoter lacking the LexA2 site, is very well induced and expressed after SOS induction. In addition, the induction profile is very similar to the one observed with the sfiA-lux fusion (FIG. 3 and FIG. 4).

recN2-4. containing the recN promoter with promoter up mutation, is very well induced and expressed after SOS induction. The total light production with this construct as well as the initial induction kinetics are even faster that those observed with pMOL890 and pMOL1067 (see FIG. 3). However, the induction pattern as illustrated by signal noise/ratio exhibits more fluctuation than for pMOL890 and pMOL1067 (see FIG. 4). Therefore this construct could be a very good candidate to detect the presence of genotoxic compounds, but appears possibly less suitable to detect the presence of individual genotoxic compounds in mixtures.

recN3-4, containing the recN promoter with promoter up mutation lacking the LexA2 site, has a very strong light production but a poor signal noise ratio. Therefore, this construct is not suitable as a genotoxicity biosensor (FIG. 3 and FIG. 4).

In another series of experiments, the dose effect curves for *E. coli* 1106 containing pMOL1066, pMOL1067, pMOL1068 or pMOL1069 were determined for MMS (concentrations from 0.5 to 128 ppm) and U.V. irradiation (irradiation time of 2 to 10 seconds). The results of these experiments are presented in the FIGS. 5 and 6.

In both experiments, the best results were obtained with pMOL1068 (recN2-4). while pMOL1069 (recN3-4) gave the lowest signal/noise ratio's. With the sfiA-lux fusion in pMOL890 similar results were obtained. Based on the results it was decided to introduce the four recN promoter-lux fusion constructs (pMOL1066-pMOL1069) as well as the sfiA-lux fusion (pMOL890) in *Salmonella typhimurium* Ames test strains TA98, TA100, TA104, TA1535 and TA1538 and to test their induction as a function of the SOS response induced by the presence of genotoxic products.

Introduction of the Promoter-lux Fusion Constructs in *S. typhimurium* and Testing All five plasmids, pMOL890 and pMOL1066 to pMOL1069, were introduced in the Ames test *S. typhimurium* strains TA98, TA100, TA104, TA1535 and TA1538. This illustrates the feasability in general of transformation of Ames test strains in general.

Mutagenicity Testing in *S. typhimurium*

In order to examen whether the introduction of pMOL890, pMOL1066, pMOL1067, pMOL1068 or pMOL1069 had any effect on the characteristics of the *S. typhimurium* strains for mutagenicity testing (determined as the reversion frequency from His– to His+ phenotype in the presence and absence of a mutagenic product), standard Ames tests were performed with both the original Ames test strains and their derivatives containing the above mentioned plasmids. For this testing the protocol described by Maron and Ames (1983) was followed. Testing was performed on MMS, 4-NQO, furazolidone, 2-AF and benzo-α-pyrene. The results are presented in the tables 1A to 1G. Not all results obtained with the original Ames tests are presented, but from the tables and the comparison between tables 1A and 1B, and 1C and 1D, it can be concluded that the introduction of the plasmids did not change the His- reversion characteristics of the recombinant strains. Consequently, the recombinant strains can be used to perform the classical Ames test.

TABLE 1A

Ames test performed on MMS with the *S. typhimurium* stains TA98, TA100, TA104, TA1535 and TA1538.

| | Number of His⁺ revertants | | | | | | | | | |
|---|---|---|---|---|---|---|---|---|---|---|
| | TA98 | | TA100 | | TA104 | | TA1535 | | TA1538 | |
| MMS 1 µl | 41 | 38 | 1120 | 1282 | 988 | 836 | 27 | 38 | 11 | 12 |
| MMS 0.2 µl | 23 | 32 | 604 | 560 | 582 | 404 | 23 | 24 | 15 | 15 |
| MMS 0.1 µl | 22 | 35 | 344 | 392 | 432 | 512 | 27 | 18 | 23 | 20 |
| Average blanks | 29 | | 146 | | 478 | | 32 | | 15 | |
| Conclusion | – | | + | | + | | – | | – | |

TABLE 1B

Ames test performed on MMS with the *S. typhimurium* stains TA98*, TA100*, TA104*, TA1535* and TA1538* that are containing pMOL890

| | Number of His⁺ revertants | | | | | | | | | |
|---|---|---|---|---|---|---|---|---|---|---|
| | TA98* | | TA100* | | TA104* | | TA1535* | | TA1538* | |
| MMS 1 µl | 22 | 27 | 536 | 528 | 672 | 724 | 29 | 26 | 29 | 27 |
| MMS 0.2 µl | 26 | 28 | 242 | 314 | 428 | 325 | 24 | 24 | 27 | 28 |
| MMS 0.1 µl | 25 | 27 | 160 | 152 | 224 | 218 | 32 | 32 | 28 | 36 |
| Average blanks | 26 | | 88 | | 100 | | 30 | | 28 | |
| Conclusion | – | | + | | + | | – | | – | |

TABLE 1C

Ames test performed on 4-NQO with the *S. typhimurium* strains TA98, TA100, TA104, TA1535 and TA1538.

| | Number of His⁺ revertants | | | | | | | | | |
|---|---|---|---|---|---|---|---|---|---|---|
| | TA98 | | TA100 | | TA104 | | TA1535 | | TA1538 | |
| 4-NQO 1 µl | 310 | 348 | 2288 | 2160 | 1520 | 1760 | 52 | 38 | 370 | 360 |
| 4-NQO 0.1 µl | 69 | 60 | 400 | 440 | 544 | 520 | 46 | 48 | 50 | 51 |
| 4-NQO 0.01 µl | 47 | 50 | 182 | 174 | 272 | 448 | 40 | 38 | 16 | 15 |
| Average blanks | 38 | | 131 | | 359 | | 45 | | 12 | |
| Average blanks with DMSO | 33 | | 125 | | 374 | | 31 | | 15 | |
| Conclusion | + | | + | | + | | – | | + | |

TABLE 1D

Ames test performed on 4-NQO with the *S. typhimurium* strains TA98*, TA100*, TA104*, TA1535* and TA1538* that are containing pMOL890.

| | Number of His⁺ revertants | | | | | | | | | |
|---|---|---|---|---|---|---|---|---|---|---|
| | TA98* | | TA100* | | TA104* | | TA1535* | | TA1538* | |
| 4-NQO 1 µl | 138 | 189 | 782 | 461 | 527 | 691 | 29 | 25 | 167 | 192 |
| 4-NQO 0.1 µl | 27 | 37 | 112 | 101 | 149 | 161 | 27 | 26 | 35 | 40 |
| 4-NQO 0.01 µl | 8 | 15 | 76 | 86 | 93 | 106 | 27 | 26 | 10 | 14 |
| Average blanks | 32 | | 69 | | 95 | | 30 | | 33 | |
| Average blanks with DMSO | 35 | | 73 | | 102 | | 28 | | 36 | |
| Conclusion | + | | + | | + | | – | | + | |

TABLE 1E

Ames test performed on furazolidone with the *S. typhimurium* strains TA98*, TA100*, TA104*, TA1535* and TA1538* that are containing pMOL890.

| | Number of His+ revertants | | | | | | | | |
|---|---|---|---|---|---|---|---|---|---|
| | TA98* | | TA100* | | TA104* | | TA1535* | | TA1538* |
| Furazolidone, 10 mmol | 26 | 30 | 532 | 544 | 640 | 620 | 49 | 38 | 17  18 |
| Furazolidone, 1 mmol | 20 | 14 | 124 | 132 | 320 | 308 | 30 | 15 | 15  7 |
| Furazolidone, 0.1 mmol | 19 | 8 | 98 | 108 | 158 | 140 | 31 | 22 | 7  9 |
| Average blanks | 12 | | 127 | | 135 | | 36 | | 9 |
| Average blanks plus DMSO | 11 | | 118 | | 157 | | 38 | | 11 |
| Conclusion | + | | + | | + | | − | | +/− |

TABLE 1F

Ames test performed on 2-AF with the *S. typhimurium* strains TA98*, TA100*, and TA104* that are containing pMOL890.

| | | | Number of His+ revertants | | | | | | |
|---|---|---|---|---|---|---|---|---|---|
| | | | TA98* | | TA100* | | TA104* | | |
| 2 AF | 670 mmol | +S9 | 5600 | 6250 | 2 | 3 | 548 | 464 | |
| 2 AF | 670 mmol | −S9 | 62 | 68 | 0 | 3 | 120 | 118 | |
| 2 AF | 67 mmol | +S9 | 3200 | 2560 | 134 | 108 | 350 | 368 | |
| 2 AF | 67 mmol | −S9 | 34 | 31 | 11 | 5 | 115 | 110 | |
| 2 AF | 67 mmol | +S9 | 576 | 555 | 73 | 52 | 178 | 162 | |
| 2 AF | 6.47 mmol | +S9 | 9 | 9 | 1 | 3 | 144 | 142 | |
| 2 AF | 6.7 mmol | +S9 | 52 | 53 | 33 | 42 | 188 | 162 | |
| Average blank + DMSO | | +S9 | 12  15 | 22 | 44  51 | 43 | 184 | 156 | 130 |
| Average blank + DMSO | | −S9 | 2  3 | 5 | 33  36 | 27 | 126 | 90 | 140 |
| Average blank | | +S9 | 17  12 | 18 | 59  39 | 45 | 180 | 192 | 172 |
| Average blank | | −S9 | 7  9 | 7 | 4  7 | 10 | 166 | 160 | 150 |
| Conclusion | | | + | | + | | + | | |

The test was performed with (+S9) as without (−S9) metabolic activation.

TABLE 1G

Ames test performed on benzo-α-pyrene with the *S. typhimurium* strains TA98*, TA100* and TA104* that are containing pMOL890.

| | | | Number of His+ revertants | | | | | | |
|---|---|---|---|---|---|---|---|---|---|
| | | | TA98* | | TA100* | | TA104* | | |
| BαP | 600 mmol | +S9 | 29 | 33 | 74 | 73 | 57 | 69 | |
| BαP | 600 mmol | −S9 | 0 | 0 | 6 | 3 | 21 | 19 | |
| BαP | 200 mmol | +S9 | 49 | 50 | 59 | 58 | 87 | 87 | |
| BαP | 200 mmol | −S9 | 0 | 0 | 7 | 23 | 26 | 32 | |
| BαP | 50 mmol | +S9 | 446 | 38 | 64 | 54 | 82 | 85 | |
| BαP | 50 mmol | +S9 | 0 | 0 | 15 | 11 | 29 | 27 | |
| BαP | 10 mmol | +S9 | 24 | 24 | 67 | 80 | 97 | 1062 | |
| Average blank + DMSO | | +S9 | 2  0 | 2 | 21  36 | 27 | 50 | 50 | 57 |
| Average blank + DMSO | | −S9 | 0  0 | 0 | 0  0 | 3 | 22 | 26 | 25 |
| Average blank | | +S9 | 0  5 | 4 | 29  25 | 28 | 49 | 78 | 41 |
| Average blank | | −S9 | 0  0 | 0 | 0  0 | 0 | 28 | 36 | 31 |
| Conclusion | | | + | | + | | + | | |

The test was performed with (+S9) as without (−S9) metabolic activation.

Luminescence Testing in *S. typhimurium*

To examine the inducibility of the different *E. coli* promoter constructs by the bacterial SOS system of *S. typhimurium*, induction experiments were performed using 64 ppm of MMS or 25.6 ppb 4-NQO, this according to the protocol disclosed further on. As control, non-induced cells were taken. The results as signal/noise ratio obtained for the recN-lux fusions pMOL1067 and pMOL1068 are presented in the FIGS. 7 and 8.

From these figures (FIG. 7 and FIG. 8) it can be concluded that the induction kinetics with pMOL1068 RecN2-4) are slightly faster than those observed for pMOL1067 (RecN1-3). but that the maximum signal/noise ratio's are higher with pMOL1067 (RecN1-3) than with pMOL1068 (RecN2-4). Therefore both constructs are of interest and complementary for genotoxicity testing. With pMOL890 (sfiA) results were found similar to those observed with pMOL1067.

The minimal detectable concentrations (MDC, in nmol/assay) were determined for 13 products. This with *S. typh-*

*imurium* Ames test strains containing pMOL890, pMOL1066, pMOL1067, pMOL1068 or pMOL1069. The results with *S. typhimurium* TA104 containing pMOL890, pMOL1066, pMOL1067, pMOL1068 or pMOL1069, and *S. typhimurium* TA98 containing pMOL890, pMOL1067 or pMOL1068 are presented in table 2. In addition literature MDC values found with the SOS chromotest and the Ames test are also presented. For certain products it was impossible to calculate the Ames test MDC values. For these products a positive (pos) or negative (neg) response is indicated.

Two products, casaminoacids and CdCl$_2$, were chosen as negative controls. It was impossible to test the casaminoacids with the Ames test, since this product contains histidine.

From table 2 it can be concluded that the best results were obtained with the strains containing pMOL890, pMOL1067 or pMOL1068. The results obtained with all constructs were always better than those found with the SOS-chromotest, this with the exception of ICR191 that gave similar results. The results were also much better than those found with the Ames test. This with the exception of 2,4,5,7-tetranitro-9-fluorenone. Therefore it can be concluded that the use of the sfiA and recN-lux gene fusions (pMOL890, pMOL1066, pMOL1067, pMOL1068 or pMOL1069) in the *S. typhimurium* Ames test strains provides a much faster and more sensitive way for detecting genotoxicity that the SOS chromotest and the Ames test.

TABLE 2 minimal detectable concentrations (MDC, in nmol/ assay) were determined for 13 products, this with *S. typhimurium* TA104 containing pMOL890, pMOL1066, pMOL1067, pMOL1068 or pMOL1069, and *S. typhimurium* TA98 containing pMOL890, pMOL1067 or pMOL1068. Literature values are also presented for the SOS chromotest and the Ames test.

MINIMAL DETECTED CONCENTRATION (MDC, in nmol/assay)

| PRODUCT | TA104 | | | | TA98 | | TA98 | TA104 | SOS chromotest | AMES |
|---|---|---|---|---|---|---|---|---|---|---|
| | pMOL1066 | pMOL1067 | pMOL1068 | pMOL1069 | pMOL1067 | pMOL1068 | pMOL890 | pMOL890 | | |
| 2-amino-fluorene | 0.44 | 0.22 | 0.22 | 0.22 | 0.44 | 0.22 | 0.14 | 0.14 | 3.56 | 0.67 |
| 2,4,5,7-tetra-nitro-9-fluorenone | 0.022 | 0.011 | 0.022 | 0.011 | 0.022 | 0.011 | 0.056 | 0.011 | 0.24 | 0.001 |
| K2Cr2O7 | 21.8 | 5.4 | 1.4 | 10.9 | 5.4 | 1.4 | 2.7 | 2.7 | 136 | 91 |
| H2O2 | 11.8 | 11.8 | 11.8 | 5.9 | 1.5 | 1.5 | 8.5 | 3.8 | 23 | neg |
| novobiocine | 1.26 | 0.32 | 1.26 | 0.32 | 0.079 | 0.63 | 0.57 | 1.26 | neg | neg |
| ICR191 | 1.1 | 0.55 | 0.55 | 1.1 | 0.28 | 0.14 | 0.14 | 0.14 | 0.13 | pos |
| chrysene | 1.095 | 0.55 | 1.095 | 0.55 | 5.5 | 5.5 | 2.2 | 2.2 | 11 | pos |
| Casamino Acids | neg | neg | neg | neg | neg | neg | neg | neg | ? | — |
| furazolidone | 0.00044 | 0.00022 | 0.00022 | 0.00044 | 0.00176 | 0.00176 | 0.00176 | 0.00176 | 0.01 | 0.1 |
| Benzo(a)-pyrene | 0.16 | 0.079 | 0.16 | 0.16 | 0.16 | 0.16 | 1.59 | 0.32 | 0.7 | 4 |
| 4-nitroquino-line-N-oxyde | 0.0034 | 0.0017 | 0.0008 | 0.0017 | 0.0017 | 0.0008 | 0.0008 | 0.0005 | 0.006 | 0.003 |
| methyl-methane-sulfonate | 7.3 | 7.3 | 7.3 | 7.3 | 7.3 | 7.3 | 7.3 | 7.3 | 20 | 60 |
| CdCl2 | neg | neg | neg | neg | neg | neg | neg | neg | neg | neg |

TABLE 3

| AGENT | OUTCOME | AMES | SOS | GROUP | NOTES |
|---|---|---|---|---|---|
| DRUGS | | | | | |
| ICR191 | | pos | pos | pos | acridine |
| Cyctophosphamide | | neg | pos | neg | antineoplastic drug |
| Mitomycin C | | pos | neg | pos | antineoplastic drug |
| Methotrexate | | pos | pos | pos | antineoplastic drug |
| ANTIMICROBIALS | | | | | |
| Furazolidone | | pos | pos | pos | antimicrobial |
| Novobiocine | | pos | pos | neg | antimicrobial |
| Carbadox | | pos | pos | pos | antimicrobial |
| Nifuroxazide | | pos | pos | pos | antimicrobial |
| Nalidixic acid | | pos | neg | pos | antimicrobial |
| PESTICIDES, HERBICIDES | | | | | |
| Ethylenethioursa | | neg | pos | neg | pesticide |
| Carbaryl | | pos | pos | pos | pesticide |
| Lindane | | neg | neg | neg | pesticide |
| Pentachlorophenole | | pos | pos | pos | herbicide |
| INORGANIC | | | | | |
| SeO2 | | pos | pos | nd | metal | oxidising agent |

TABLE 3-continued

| AGENT | OUTCOME | AMES | SOS | GROUP | NOTES |
|---|---|---|---|---|---|
| ZnCl2 | neg | neg | neg | metal | industrial |
| CdCl2 | neg | neg | neg | metal | industrial |
| K2Cr2O7 | pos | pos | pos | metal | oxidising agent |
| H2O2 | pos | neg | pos | peroxide | oxidising agent |
| Sodiumazide | pos | pos | neg | azide | industrial |
| PAH | | | | | |
| Benzo(a)pyrene | pos | pos | pos | PAH(pentacyclic) | env. pollutant |
| Chrysene | pos | pos | pos | PAH(pentacyclic) | env. pollutant |
| Naphtalene | neg | neg | neg | PAH(pentacyclic) | env. pollutant |
| Pyrene | pos | neg | pos | PAH(pentacyclic) | env. pollutant |
| 2,4,5,7-tetranitro-9- fluorenone | pos | pos | pos | PAH(tricyclic) | env. pollutant |
| 4-Nitroquinoline-N-oxyde | pos | pos | pos | PAH(tricyclic) | env. pollutant |
| Fluoranthene | pos | pos | pos | PAH(tricyclic) | env. pollutant |
| Anthracene | neg | neg | neg | PAH(tricyclic) | env. pollutant |
| Phenanthrene | pos | neg | pos | PAH(tricyclic) | env. pollutant |
| LAB CHEMICALS | | | | | |
| N-Nitrosodiethylamine | pos | pos | pos | nitrosamine | |
| 2-Aminofluorene | pos | pos | pos | arom. amine | |
| Casaminoacids | neg | nf* | neg | amino acids | |
| Sodium Dodecyl Sulphate | neg | neg | neg | anionic detergent | |
| Glucose | neg | neg | neg | sugar | |
| Methylmethanesulphonate | pos | pos | pos | sulphonate | |
| Ethylmethanesulphonate | pos | pos | pos | sulphonate | |
| *not feasible (histidine) | | | | | |
| SOLVENT, FUEL, ... | | | | | |
| Hydrazine | pos | pos | pos | hydrazine | rocket fuel |
| Epichlorohydrine | pos | pos | pos | expoxypropane | solvent |
| ELECTROMAGNETIC | | | | | |
| UV-rays | pos | pos | nd | EM | therapeutic, sun, .. |
| RX-rays | pos | pos | pos | EM | therapeutic |

Table 3 presents the results of genotoxicity tests performed with the TA 98 and TA104 strains containing pMOL1067 or pMOL1068. since the results found with these strains were similar, only the final outcome of the tests is presented (positive or negative). Similar results are given for the SOS chromotest (SOS) and the Ames test. The agents tested were generally accepted representative agents from the following categories: drugs, antimicrobial agents, pesticides, herbicides, inorganic compounds, polyaromatic hydrocarbons, laboratory chemicals, solvents, fuel and electromagnetic rays. From this table it can be concluded that the hybrid TA Ames test strains can be used to detect genotoxicity for all categories of products tested, and that only a few differences are observed with the results found for the SOS chromotest and the Ames test.

When comparing the results obtained with the TA98 and TA104 strains containing pMOL890, pMOL1067 or pMOL1068, with the results obtained with the SOS chromotest it can be concluded that: When a product is negative in the test with the TA98 and TA104 strains containing pMOL890, pMOL1067 or pMOL1068, it is also negative with the SOS chromotest. However, novobiocine and sodiumazide which are potentially genotoxic were negative in the SOS chromotest but positive in the test with the TA98 and TA104 strains containing pMOL890, pMOL1067 or pMOL1068. Therefore one can conclude that the test with the TA 98 and TA104 strains containing pMOL890, pMOL1067 or pMOL1068 is more accurate for genotoxicity testing than the SOS chromotest, since no false-negatives were obtained. When a product is negative in the test with the TA98 and TA104 strains containing pMOL890, pMOL1067 or pMOL1068, it is also negative with the Ames test. The only exceptions were cyclophosphamide and ethylenethiourea that were negative in the test with the TA98 and TA104 strains containing pMOL890, pMOL1067 or pMOL1068. This is however not surprising, since these products do not induce the bacterial SOS response.

False-negative genotoxic products in the Ames test, like mitomycin C, naladixic acid, hydrogen-peroxide, pyrene and phenanthrene, were found to be positive in the test with the TA98 and TA104 strains containing pMOL890, pMOL1067 or pMOL1068. Therefore one can conclude that the test with the TA98 and TA104 strains containing pMOL890, pMOL1067 or pMOL1068 is not merely as good as the Ames test, but is in addition more accurate for the testing of environmental contaminants like PAH's.

Testing of Combinations of Genotoxic Products

The reaction of the different constructs when more than one genotoxic product is present in the test sample, was examined. This is an important aspect, since environmental samples often contain more than one genotoxic pollutant. Also in this regard many pharmaceutical products that have to be tested for genotoxicity can be a combination of different active genotoxic substances (e.g. anticancer or anti AIDS drugs). The experiments were performed with TA98 and TA104 containing either pMOL1067 or pMOL890. These two constructs were chosen since they show similar induction kinetics and the best signal/noise ratio's in *S. typhimurium* (see FIG. 7 and FIG. 8). As test products, several combinations of MMS and novobiocine were taken. These products were used since they were found by us to have different induction kinetics (e.g., with pMOL1067 MMS gives a maximum after 2 hours, while the maximal signal/noise ratio with novobiocine is observed after 4 hours). Examples of the results of these experiments are presented in FIGS. 9 and 10.

From these results it can be concluded that with both strains containing pMOL890 (sfiA-lux) or pMOL1067

(recN1,3-lux) the presence of at least two individual genotoxic compounds can be determined in a mixture of genotoxic compounds. This was completely contrary to expectations, because an increase of the maximum signal instead of two individual maxima was to be expected.

It was also examined if the data obtained in the previous experiment with combinations of MMS and novobiocine would result in a genotoxicity ranking for the different combinations used, and if the ranking would be the same with the different test strains [e.g. with TA98 (pMOL1067) and TA104 (pMOL890)]. To test this, the total signal/noise ratio was calculated for each of the combinations tested, and subsequently they were ranked from low to high. This resulted in a logical and identical ranking for the different test strains. An example is shown in the FIGS. 11 and 12.

Toxicity Testing

The different constructs produce a background light signal in the absence of a genotoxic product. This is called the noise. This noise signal can be used as a measure for the presence of a toxic instead of a genotoxic compound. Especially the strains containing pMOL890 and pMOL1068 that show a relatively high noise are considered very suitable for this toxicity testing (their noise will go up in the course of a 4 hour experiment from 100 to 13000 relative light units), while strains containing pMOL1066 or pMOL1067 that have a low noise are of less use (their noise will go up in the course of a 4 hour experiment from 20 to 750 relative light units). This is illustrated in FIGS. 13 and 14, where the decrease in light production was observed for TA98 containing pMOL1067 or pMOL1068 when challenged with different concentrations of the toxic product R116.

By comparing FIGS. 13 and 14 it is evident that the signal/noise ratio's found with TA98 (pMOL1068) are much more constant than those found for TA98 (pMOL1067). As a consequence of the much higher basic light production for strain TA98 (pMOL1068) the importance of errors in the measurement of the light production is less, resulting in less fluctuation in the calculated signal/noise data. Strain TA98 (pMOL1068) but also other strains containing pMOL890 or pMOL1068 are very useful for the IC50 calculation value of toxic products. Preferred strains will exhibit at least the same basic light production as strain TA 98 (pMOL1068)

Testing of Environmental Samples

Since testing on pure products showed that strains containing pMOL890, pMOL1067 or pMOL1068 were more sensitive for the testing of potential environmental contaminants (like PAH's) than the classical Ames test, these strains were used for the testing of environmental samples. Examples presented are:

evaluation of the bioremediation of soil polluted with PAH's appearance of water soluble PAH degradation products Soil samples were polluted with 500 ppm mixture (Borneff mixture containing naphthalene, phenanthrene, anthracene, fluoranthene, pyrene and benzo-α-pyrene). Subsequently the soil was treated in a bioreactor to stimulate the bacterial degradation of the PAH's. To evaluate the bioremediation of the soil and to examine the decrease in genotoxicity. 10 g soil samples were taken during a period of 3 weeks. These samples were extracted with hexane (1 ml/g soil) and the extracts were concentrated 100×. The concentrated extracts were diluted 1 to 8 times and used for genotoxicity testing (with and without metabolic activation). For each sample a genotoxicity value was calculated as the product of (signal/noise ratio higher than 2 at the highest positive dilution)×(dilution factor). For instance, if at dilution 4× a S/N ratio of 2.8 was found, this sample received 11.2 as genotoxicity value. The genotoxicity values were plotted and this gave a nice overview and evaluation of the genotoxicity of the polluted soil. Data of such an experiment are presented in FIG. 15.

From FIG. 15 it can be concluded that in time there is a decrease of the genotoxicity of the soil polluted with PAH's. This demonstrates that the strains containing pMOL890, pMOL1067 or pMOL1068 are very useful for the follow up and evaluation of the remediation of soil polluted with genotoxic products. In general strains comprising a sequence with an SOS regulated promoter with an induction ratio higher than 40, said promoter being operatively linked to a reporter encoding nucleic acid sequence encoding a reporter resulting in a signal that can be assayed as light production can be used in a preferred embodiment. Any of the claimed host microorganisms can be suitably used in such a test.

To analyze the formation of water soluble intermediate PAH degradation products, the degradation of phenanthrene, fluorene and fluoranthene was examined. To do so, minimal M9 medium without extra carbon source was saturated with 0.1% of the PAH and inoculated with a strain capable of degrading the PAH. Every 3 days samples (200 ml) were taken and concentrated according to the procedure of Grifoll et al (1994). The extraction occurred at pH 2.5 or pH 7 and the samples were concentrated to 5 ml. 1 ml of each sample was dried out at 37° C. and resuspended in 100 $\mu$l DMSO. 1 $\mu$l of this was used for genotoxicity testing. For phenanthrene an increase followed by a decrease in genotoxicity was observed, for fluorene no significant increase in genotoxicity was observed, but for fluoranthene an increase of genotoxicity was observed. This indicated the formation and accumulation of a genotoxic intermediate compound. The result of the evaluation of fluoranthene degradation by strain LB208 is presented in FIG. 16. Only the data for the extractions performed at pH 2.5 are presented.

From this experiment it can be concluded that strains containing pMOL890, pMOL1067 or pMOL1068 are useful for the evaluation of the degradation of genotoxic pollutants and for the appearance and accumulation of genotoxic intermediate degradation products. In general strains comprising a sequence with an SOS regulated promoter with an induction ratio higher than 20, preferably higher than 40, most preferably higher than 50, said promoter being operatively linked to a reporter encoding nucleic acid sequence encoding a reporter resulting in a signal that can be assayed as light production can be used in a preferred embodiment. Any of the claimed host microorganisms can be suitably used in such a test. Toxicity testing was also possible on environmental samples as was demonstrated on DMSO extracts of gazoline polluted soil. Higher concentrations of the extract resulted in increased toxicity (data not shown).

Standard Operating Protocol for Testing Genotoxicity with the recN-lux Bacteria

1. Introduction

The test is based on bacteria that contain the lux operon of *Vibrio fischeri* under transcriptional control of the recN gene, that is part of the SOS-system. After incubation of the cells with a genotoxic product, the recN promoter will become derepressed, resulting in expression of the lux operon. The expression results in light production in function of the genotoxicity. However, the same protocol can also be used for the test performed with the sfiA-Lux strans. For other SOS regulated promoter comprising systems according to the invention a person skilled in the art will also be able to use this protocol.

2. Strains
   TA104 recN1-3
   TA104 recN2-4
   TA98 recN1-3
   TA98 recN2-4
3. Materials
   3.1 Media
      3.1.1 Medium 869(pH=7)
         per liter desionised H2O
         tryptone 10 g
         yeast extract 5 g
         NaCl 5 g
         glucoseD 1 g
         $CaCl_2.2H_2O$ 0.345 g
         cysteine 30 mg
      The medium is sterilised by autoclaving for 20 min. at 120° C. Tetracycline (20 μg/ml) and ampicillin (100 μg/ml) are added. The medium is stored at 4° C.
      3.1.2 Poor 869 medium(pH=7)
         per liter deionised H2O
         tryptone 2 g
         yeast extract 1 g
         NaCl 5 g
         glucoseD 1 g
         $CaCl_2.2H_2O$ 0.345 g
         cysteine 30 mg
   3.2 S9 components
      3.2.1 S9
   The Arochlor-induced microsomal fraction S9 from rat liver is obtained using a standard protocol. It can be obtained from a pharmaceutical factory.
      3.2.2 KCl/MgCl2 solution
         KCl 6.15 g
         $MgCl_2.6H_2O$ 4.7 g
         dist. $H_2O$ to 100 ml
         Autoclave and store at room temp.
      3.2.3 0.1M β-NADP
         β-NADP 500 mg
         sterile dist. $H_2O$ 6.53 ml
         store 500 μl portions in cryotubes at −20° C.
      3.2.4 1M glucose-6-phosphate (G6P)
         G6P 282 mg
         sterile dist. $H_2O$ 1 ml
         store in cryotube at −20° C.
      3.2.5 Phophate buffer 0.2M (pH=7.4)
         60 ml 0.2M $NaH_2PO_4.H_2O$
         440 ml 0.2M $Na_2HPO_4$
         adjust the pH to 7.4 and autoclave 100 ml portions
         store at room temperature
   3.3 Chemicals
      DMSO: solvent for hydrophobic products
      MMS: positive control for testing without metabolisation
      4NQO: positive control for testing hydrophobic products without metabolisation
      2AF: positive control for testing with S9 metabolisation
   3.4 Equipment
96-well microplate luminometer, witch is computer controlled with storage of the data in a spreadsheet.
4. Test Procedure
   4.1 Maintainance and starting of the culture
      4.1.1 Maintainance
   Scrape off a little of the frozen permanent and inoculate 25 ml 869 medium (see 3.1.1). Incubate overnight (ON) at 37° C. on a rotative shaker (170 RPM). The next morning 2.5 ml of DMSO are added. The bacterial suspension is dispensed in cryotubes and kept at −80° C. One tube is used for testing the bacteria as recommended for the Ames strains (rfa, pKM101, etc).
      4.1.2 Starting the test culture
   Inoculate 5 ml of medium 869 (see3.1.1) with 40 μl of the bacterial stock (see 4.1.1) and incubate ON at 37° C. on a rotative shaker (170 RPM). Next morning 20 μl of the ON culture are inoculated in 2.5 ml poor 869 (see 3.1.2). Incubate 1 houre at 37° C. with shaking (170 RPM).
   4.2 Dilutions of the test product
      4.2.1 Stock solution
   The concentration of the stock solution is chosen in function of the solubility and the required highest concentration. Weigh a few mg (Amg) in a vial and add the required volume(Vml) of solvent to obtain the desired concentration (Smg/ml), with the formula V=A/S.
      4.2.2 Dilution of the test product
         Add to 8 vials(#1 to 8) 50 μl of the solvent($H_2O$ or DMSO).
         Add to 1 vial (#9) 100 μl of the stock solution.
         Transfer 50 μl from vial #9 to vial #8, mix 5× with a pipet and transfer 50 μl to vial #7, etc . . . to vial #2. After mixing 50 μl are discarded from vial #2.
         Add to each vial 450 μl poor 869.
      Transfer 10 μl of each vial to the 96-well plate:
         from vial #1 to the colums 1.2 and 3 (=solvent control)
         from vial #2 to colum 4, from vial #3 to colum 5, etc . . . to colum 11
      4.2.3 Preparation of the positive control
         For the application see section 3.3 2AF(8 ppm): make a solution of 6400 ppm in DMSO; dilute ½ in 50 μl DMSO to 800 ppm; add 450 μl of poor 869 (=80 ppm); transfer 10 μl to the wells E12, F12, G12, H12.
         4NQO(4 ppb): make a solution of 1000 ppm in DMSO; to 40 μl of this add 960 μl DMSO(=40 ppm); add to 10 μl of this 990 μl DMSO (=0.4 ppm); to 50 μl of the 0.4 ppm solution add 450 μl poor 869 (=40 ppb); transfer 10 μl to the wells A12, B12, C12, D12.
         MMS(16 ppm): add 5 μl MMS to 995 μl H2O (=6400 ppm); dilute ½ in 50 μl to 1600 ppm; Add 450 μl poor869 to 50 μl of this 1600 ppm solution; Transfer 10 μl to the wells A12, B12, C12, D12.
   4.3 Experiment with or without S9mix
      4.3.1 With S9mix
   The S9mix is always prepared freshly before adding to the bacteria.
   Mix gently in a tube:
      100 μl $KCl:MgCl_2$ (3.2.2)
      100 μl β-NADP (3.2.3)
      50 μl G6P (3.2.4)
      2500 μl phosphate buffer (3.2.5)
      2500 μl poor 869 (3.1.2)
      132 μl S9
   Adding the bacteria
   mix gently:
      140 μl of the bacterial suspension (4.1.2)
      860 μl poor 869
      400 μl S9mix
   Transfer 90 μl to
      wells E1 to E12: TA104 recN1-3
      wells F1 to F12: TA104 recN2-4 wells G1 to G12: TA98 recN1-3
wells H1 to H12: TA98 recN2-4
4.3.2 WITHOUT S9mix
add 1260 µl poor 869 to 140 µl of the bacterial suspension (4.1.2) transfer 90 µl to the wells:
wells A1 to A12: TA104 recN1-3
wells B1 to B12: TA104 recN2-4
wells C1 to C12: TA98 recN1-3
wells D1 to D12: TA98 recN2-4

5. Measuring

Put the 96-well plate into the luminometer and start measuring (1 sec/well; cycletime of 300 sec; 60 cycles; 30° C.)

6. Calculation

After finishing the measurements, the data are saved in a worksheetformat. This block of data is transferred to a macro sheet that automatically calculates the signal to noise ratios, makes graphs and the final report.

7. Evaluation

A product is considered to be genotoxic when:
1) The signal to noise ratio is equal to or higher than 2 for at least 2 concentrations
2) There is a clear dose-effect response References Beck, E., and Bremer, E. (1980). Nucleotide sequence of the gene ompA coding the outer membrane protein II* of *Escherichia coli* K12, Nucleic Acids Research 8: 3011–3027

Finch, P. W., Chambers, P. and Emmerson, P. T. 1985, Identification of the *Escherichia coli* recN gene product as a major SOS protein. J. Bacteriol. 164; 653–658

Gee, P. Maron, D. M., and Ames, B. N. (1994) Detection and classification of mutagens: a set of base-specific Salmonella tester strains. Proc. Natl. Acad. Sci. USA 91: 11606–11610.

Grifoll, M. Selifonov, S. A. and Chapman, P. J. (1994), Evidence for a novel pathway in the degradation of fluorene by Pseudomonas sp. strain F274. Appl. Environ. Microbiol. 60: 2438–2449

Maron, D. M. and Ames, B. N. (1983), Revised Methods for the Salmonella mutagenicity test. Mutation Research 113: 173–215

Murray, N. E., Brammar, W. J. and Murray, K. (1977). Lambdoid phages that simplify the recovery of in vitro recombinants. Mol. Gen Genet. 150: 53–61.

Oda, Y., Nakamura, S., Oki, I, Kato, T., and Stinagawa, H. (1985). Evaluation of a new system (umu-test) for the detection of environmental mutagens and carcinogens. Mutation Research: 147: 219–229.

Peterson, K. R. and Mount, D. W. (1987). Differential repression of SOS genes by unstable LexA41 (Tsl-1) protein causes a split-phenotype in *Escherichia coli* K12, J. Mol. Biol. 193, 27–40.

Picksly, S. M. Morton, S. J. and Lloyd, R. G. (1985). The recN locus of *Escherichia coli* K12: Molecular analysis and identification of the gene product. Mol. Gen. Genet. 201: 301–307.

Quillardet, P. Huisman, O., D'Ari, R. and Hofnung. M. (1982). SOS chromotest, a direct assay of induction of an SOS function in *Escherichia coli* K12 to measure genotoxicity. Proc. Nat. Acad. Sci. USA 79: 5971–5975.

Rostas, K., Morton, S. J., Picksley, S. M. and Lloyd, R. G. (1987). Nucleotide sequence and LexA regulation of the *Escherichia coli* recN gene. Nucleic Acids Research 15: 5041–5049.

Schnarr, M., Oertel-Buchheit, P., Karmaier, M. and Granger-Schnarr, M. (1991), DNA binding properties of the LexA repressor, Biochemie, 73, 423–431.

What is claimed is:

1. A recombinant nucleic acid sequence comprising an SOS regulated promoter with an induction ratio higher than 40, said promoter being operatively linked to a reporter encoding flucleic acid sequence encoding a reporter resulting in a signal that can be assayed as light production, wherein the promoter is selected from the group consisting of RecN and mutated RecN.

2. A recombinant nucleic acid sequence according to claim 1, wherein the promoter comprises a mutation improving promoter strength or regulation, said mutation not destroying the SOS regulation.

3. A recombinant nucleic acid sequence according to claim 1, wherein the promoter comprises at least one active LexA binding site and has a mutation in at least one other LexA binding site.

4. A recombinant nucleic acid sequence according to claim 1, wherein the promoter comprises a promoter up mutation.

5. A recombinant nucleic acid sequence according to claim 1, wherein the promoter comprises a promoter up mutation in the −35 region of said promoter.

6. A recombinant nucleic acid sequence according to claim 1, wherein the reporter encoding nucleic acid sequence comprises the luciferase A and B genes.

7. A recombinant nucleic acid sequence according to claim 1, wherein the reporter encoding nucleic acid sequence comprises the luciferase A and B genes and the luciferase C, D and E genes required for producing the limiting fatty acid substrate that is used in recycling.

8. A host microorganism comprising a recombinant nucleic acid sequence according to claim 1.

9. A host microorganism according to claim 8, said host microorganism being an *E. coli*.

10. A host microorganism according to claim 8, said host microorganism being a *Salmonella typhimurium*.

11. A host microorganism according to claim 10, said host mircoorganism being selected from TA98, TA100, TA102, TA104, TA1535, TA1538, TA7001 to TA7006, and TA7041 to TA7046.

12. A method for determining the presence of a toxic compound in a sample, said method comprising the steps of culturing a host microorganism, said host microorganism being a host microorganism according to claim 8, measuring the luminescence of the culture and determining whether the luminescence of the culture has changed, decreased luminescence being indicative of the presence of a toxic compound.

13. A method for determining the presence of multiple genotoxic compounds in a sample, said method comprising the steps of culturing a host mircoorganism, said host microorganism comprising a nucleic acid sequence comprising an SOS regulated promoter, said promoter being operatively linked to a reporter encoding nucleic acid sequence encoding a reporter resulting in a signal that can be assayed as light production, measuring luminescence of the culture, said measuring occurring at various points in time, and determining the signal to noise ratio at said points in time, plotting the data, said data representing the kinetics of genotoxicity of said sample with multiple peaks being indicitive of multiple genotoxicity compounds with different induction kinetics.

14. A method according to claim 13, wherein the host microorganism comprises a recombinant nucleic acid sequence comprising an SOS regulated promoter with an induction ratio higher than 40, wherein the promoter is operatively linked to a reporter encoding nucleic acid sequence encoding a reporter resulting in a signal that can be assayed as light production.

15. A method for determining the presence of a genotoxic compound in a sample, said method comprising the steps of culturing a host microorganism, said host microorganism comprising a nucleic acid sequence comprising an SOS regulated promoter with an induction ratio higher than 20, said promoter being operatively linked to a reporter encoding nucleic acid sequence encoding a reporter resulting in a signal that can be assayed as light production, measuring the luminescence of the culture at multiple points in time, preferably continuously and determining whether the luminescence of the culture has changed, increased luminescence being indicative of the presence of a genotoxic compound.

16. A method for determining the kinetics of genotoxicity of a sample, said method comprising culturing a host mircoorganism, said host microorganism comprising a nucleic acid sequence comprising an SOS regulated promoter with an induction ratio higher than 20, said promoter being operatively linked to a reported encoding nucleic acid sequence encoding a reporter resulting in a signal that can be assayed as light production, measuring luminescence of the culture at multiple points in time and determining the signal to noise ratio of the luminescence at said points in time and plotting the luminescence signal to noise data, said plot representing the kinetics of genotoxicity of said sample.

17. A method for determining both the presence of genotoxic compounds in a sample in a sample and mutagenicity of a sample, said method comprising culturing a host microorganism, said host microorganism comprising a nucleic acid sequence comprising an SOS regulated promoter, said promoter being operatively linked to a reporter encoding a nucleic acid sequence encoding a reporter resulting in a signal that can be assayed as light production, wherein the host microorganism comprises a recombinant nucleic acid sequence comprising an SOS regulated promoter with an induction ratio higher than 40, said promoter being operatively linked to a reporter encoding nucleic acid sequence encoding a reporter resulting in a signal that can be assayed as light production, measuring the luminescence of the culture, said measuring occurring at various points in time, and determining the signal to noise ratio at said points in time, plotting the data, said data representing the kinetics of genotoxicity of said sample with multiple peaks being indicative of multiple genotoxicity compounds with different induction kinetics, and performing a classical Ames test.

\* \* \* \* \*